(12) United States Patent
Woods et al.

(10) Patent No.: US 6,306,639 B1
(45) Date of Patent: Oct. 23, 2001

(54) GENETICALLY MODIFIED CYANOBACTERIA FOR THE PRODUCTION OF ETHANOL, THE CONSTRUCTS AND METHOD THEREOF

(75) Inventors: Robert Paul Woods; John Robert Coleman, both of Markham; Ming De Deng, North York, all of (CA)

(73) Assignee: Enol Energy Inc. (CA)

( * ) Notice: Subject to any disclaimer, the term of this patent is extended or adjusted under 35 U.S.C. 154(b) by 0 days.

(21) Appl. No.: 09/026,845

(22) Filed: Feb. 20, 1998

Related U.S. Application Data

(63) Continuation-in-part of application No. 08/801,331, filed on Feb. 19, 1997, now abandoned.

(51) Int. Cl.⁷ .............................. C12N 1/20; C07H 21/02; C07H 21/04
(52) U.S. Cl. ................... 435/252.3; 536/23.1; 536/23.2; 536/24.1
(58) Field of Search ................ 435/252.3; 536/23.1, 536/23.2, 24.1

(56) References Cited

U.S. PATENT DOCUMENTS

| | | | |
|---|---|---|---|
| 4,778,759 | * 10/1988 | Szalay et al. .................. | 435/172.3 |
| 5,000,000 | * 3/1991 | Ingram et al. .................. | 435/161 |
| 5,028,539 | 7/1991 | Ingram et al. .................. | 435/161 |

OTHER PUBLICATIONS

Soltes–Rak, E. et al., Appl. Env. Miro., vol. 59, No. 8, pp. 2404, Aug. 1993.*
Ronen–Tarazi, M. et al., Plant Physiol., vol. 108, pp. 1461–1469, Aug. 1995.*
Gruber et al., Cur. Micro., vol. 22, pp. 15–19, 1991.*
Plant Physiol. (1995) 108: 1461–1469 Michael Ronen–Tarazi, et al. The Genomic Region of rbcLS in Synechococcus sp. PCC 7942 Contains Genes Involved in the Ability to Grow under Low $CO_2$ Concentration and in Chlorophyll Biosynthesis 1.
Applied and Environmental Microbiology, Aug. 1993, p. 2404–2410 vol. 59, No. 8 Erika Soltes–Rak, et al Effect of Promoter Modification on Mosquitocidal cryIVB Gene Expression in Synechococcus sp. Strain PCC 7942.

* cited by examiner

*Primary Examiner*—Ponnathapu Achutamurthy
*Assistant Examiner*—Peter P. Tung
(74) *Attorney, Agent, or Firm*—Michael Best & Friedrich LLP

(57) ABSTRACT

The invention relates to the genetic modification of Cyanobacteria for the production of ethanol, and more particularly, to the genetic modification of Cyanobacteria by incorporating the genetic information encoding for pyruvate decarboxylase (pdc) and alcohol dehydrogenase (adh).

11 Claims, 22 Drawing Sheets

*Synechococcus* PCC 7942 cells transformed with the vector pCB4-CPpa were first grown at 30oC and then transferred to 42 °C. Cells were harvested at intervals todetermine the activity of pyruvate decarboxylase.

Synechococcus PCC 7942 Wt cells and the cells transformed with the shuttle vector pCB4-Rpa were grown in a liquid batch culture. The culture was sampled at intervals to assay the amount of ethanol. The bars indicate the S.D. for 4-6 different samples

FIG. 9(1)

```
LOCUS       ZMOPDC      1905 bp ds-DNA        BCT     30-JUN-1987
DEFINITION  Zymomonas mobilis pyruvate decarboxylase (pdc) gene, complete cds.
ACCESSION   M15393
KEYWORDS    decarboxylase; pyruvate decarboxylase.
SOURCE      Z.mobilis (strain CP4) DNA, clone pLOI275, subclone pLOI276.
  ORGANISM  Zymomonas mobilis
            Prokaryotae; Facultative anaerobic gram-negative rods.
REFERENCE   1 (bases 1 to 1905)
  AUTHORS   Conway,T., Osman,Y.A., Konnan,J.I., Hoffmann,E.M. and Ingram,L.O.
  TITLE     Promoter and nucleotide sequences of the Zymomonas mobilis pyruvate
            decarboxylase
  JOURNAL   J. Bacteriol. 169, 949-954 (1987)
  MEDLINE   87137309
COMMENT     Computer-readable copy of sequence in [1] kindly provided by
            T.Conway (27-APR-1987).
            There is a potential ribosome binding region at bases 189-192.

NCBI gi: 155597
FEATURES            Location/Qualifiers
     source         1..1905
                    /organism="Zymomonas mobilis"
     mRNA           153..>1878
                    /note="pdc mRNA"
     CDS            199..1878
                    /note="pyruvate decarboxylase (E.C 4.1.1.1); NCBI gi:
                    155598"
                    /codon_start=1
```

/translation="MSYTVGTYLAALVQIGLKHHFAVAGDYNLVLLDNLLLNKNMEQV

YCCNELNCGFSAEGYARAKADAAAVVTYSVGALSAFDAIGGAYAENLPVILISGAPNN

NDHAAGHVLHHALGKTDYHYQLEMAKNITAAAEAIYTPEEAPAKIDHVIKTALREKKP

VYLEIACNIASMPCAAPGPASALFNDEASDEASLNAAVEETLKFIANRDKVAVLVGSK

LRAAGAEEAAVKFADALGGAVATMAAAKSFFQKKTALHRYLMGEVSYPGVEKTMKEAD

AVIALAPVFNDYSTTGWTDIPDPKKLVLAEPRSVVVNGVRFPSVHLKDYLTRLAQKVS

KKTGALDFFKSLNAGELKKAAPADPSAPLVNAEIARQVEALLTPNTTVIAETGDSWFN

AQRMKLPNGARVEYEMQWGHIGWSVPAAFGYAVGAPERRNILMVGDGSFQLTAQEVAQ

FIG. 9(2)

MVRLKLPVIIFLINNYGYTIEVMIHDGPYNNIKNWDYAGLMEVFNGNGGYDSGAGKGL
KAKTGGELAEAIKVALANTDGPTLIECFIGREDCTEELVKWGKRVAARQQP"
BASE COUNT    467 a   489 c   473 g   476 t
ORIGIN    106 bp upstream of DraI site.

```
   1 tatcgctcat gatcgcgaca tgttctgata ttttcctcta aaaaagataa aaagtctttt
  61 cgcttcggca gaagaggttc atcatgaaca aaaattcggc atttttaaaa atgcctatag
 121 ctaaatccgg aacgacactt tagaggtttc tgggtcatcc tgattcagac atagtgtttt
 181 gaatatatgg agtaagcaat gagttatact gtcggtacct atttagcggc gcttgtccag
 241 attggtctca agcatcactt cgcagtcgcg ggcgactaca acctcgtcct tcttgacaac
 301 ctgcttttga acaaaaacat ggagcaggtt tattgctgta acgaactgaa ctgcggttc
 361 agtgcagaag gttatgctcg tgccaaagcg gacgcagcag ccgtcgttac ctacagcgtc
 421 ggtgcgcttt ccgcatttga tgctatcggt ggcgcctatg cagaaaacct tccggttatc
 481 ctgatctccg gtgctccgaa caacaatgat cacgctgctg gtcacgtgtt gcatcacgct
 541 cttggcaaaa ccgactatca ctatcagttg gaaatggcca agaacatcac ggccgcagct
 601 gaagcgattt acaccccaga agaagctccg gctaaaatcg atcacgtgat taaaactgct
 661 cttcgtgaga agaagccggt ttatctcgaa atcgcttgca acattgcttc catgccctgc
 721 gccgctcctg gaccggcaag cgcattgttc aatgacgaag ccagcgacga agcttctttg
 781 aatgcagcgg ttgaagaaac cctgaaattc atcgccaacc gcgacaaagt tgccgtcctc
 841 gtcggcagca agctgcgcgc agctggtgct gaagaagctg ctgtcaaatt tgctgatgct
 901 ctcggtggcg cagttgctac catggctgct gcaaaaagct tcttccagaa gaaaaccgca
 961 ttacatcggt acctcatggg tgaagtcagc tatccgggcg ttgaaaagac gatgaaagaa
1021 gccgatgcgg ttatcgctct ggctcctgtc ttcaacgact actccaccac tggttggacg
1081 gatattcctg atcctaagaa actggttctc gctgaaccgc gttctgtcgt cgttaacggc
1141 gttcgcttcc ccagcgttca tctgaaagac tatctgaccc gtttggctca gaaagtttcc
1201 aagaaaaccg gtgctttgga cttcttcaaa tccctcaatg caggtgaact gaagaaagcc
1261 gctccggctg atccgagtgc tccgttggtc aacgcagaaa tcgcccgtca ggtcgaagct
1321 cttctgaccc cgaacacgac ggttattgct gaaaccggtg actcttggtt caatgctcag
1381 cgcatgaagc tcccgaacgg tgctcgcgtt gaatatgaaa tgcagtgggg tcacatcggt
1441 tggtccgttc ctgccgcctt cggttatgcc gtcggtgctc cggaacgtcg caacatcctc
1501 atggttggtg atggttcctt ccagctgacg gctcaggaag tcgctcagat ggttcgcctg
1561 aaactgccgg ttatcatctt cttgatcaat aactatggtt acaccatcga agttatgatc
1621 catgatggtc cgtacaacaa catcaagaac tgggattatg ccggtctgat ggaagtgttc
1681 aacggtaacg gtggttatga cagcggcgct ggtaaaggcc tgaaggctaa aaccggtggc
1741 gaactggcag aagctatcaa ggttgctctg gcaaacaccg acggcccaac cctgatcgaa
1801 tgcttcatcg gtcgtgaaga ctgcactgaa gaattggtca atggggtaa gcgcgttgct
1861 gcccgccaac agccgtaagc ctgttaacaa gctcctctag ttttt
//
```

FIG. 10 (1)

```
<TITLE>GenBank Database Document Reader</TITLE>
<BODY BGCOLOR="#ffffe8"><PRE>

LOCUS       ZMOADHB      1747 bp    DNA            BCT       15-SEP-1989
DEFINITION  Z.mobilis alcohol dehydrogenase II (AdhB) gene, complete cds.
ACCESSION   M15394
NID         g155576
KEYWORDS    alcohol dehydrogenase II.
SOURCE      Z.mobilis (CP4) DNA, clone pLOI287.
  ORGANISM  Zymomonas mobilis
            Eubacteria; Proteobacteria; alpha subdivision; Zymomonas group;
            Zymomonas.
REFERENCE   1  (bases 1 to 1747)
  AUTHORS   Conway,T., Sewell,G.W., Osman,Y.A. and Ingram,L.O.
  TITLE     Cloning and sequencing of the alcohol dehydrogenase II gene from
            Zymomonas mobilis
  JOURNAL   J. Bacteriol. 169, 2591-2597 (1987)
  MEDLINE   87222181
COMMENT     Draft entry and computer-readable copy of sequence in [1] kindly
            provided by T.Conway (27-APR-1987).
            The Z.mobilis AdhII is an Fe-containing Adh peptide and shows 53.5%
            homology with the Adh4 of yeast (V.Williamson, UC Davis). There
            are tandem promoters located upstream of the transcription
            initiation sites.
FEATURES             Location/Qualifiers
     source          1..1747
                     /organism="Zymomonas mobilis"
                     /db_xref="taxon:542"
     mRNA            156..1634
                     /note="adhB mRNA (alt.)"
     mRNA            256..1634
                     /note="adhB mRNA (alt.)"
     CDS             432..1583
                     /note="alcohol dehydrogenase II (EC 1.1.1.1)"
                     /codon_start=1
                     /db_xref="PID:g155577"
                     /transl_table=11
```

/translation="MASSTFYIPFVNEMGEGSLEKAIKDLNGSGFKNALIVSDAFMNK

SGVVKQVADLLKAQGINSAVYDGVMPNPTVTAVLEGLKILKDNNSDFVISLGGGSPHD

CAKAIALVATNGGEVKDYEGIDKSKKPALPLMSINTTAGTASEMTRFCIITDEVRHVK

MAIVDRHVTPMVSVNDPLLMVGMPKGLTAATGMDALTHAFEAYSSTAATPITDACAL
K

FIG. 10 (2)

AASMIAKNLKTACDNGKDMPAREAMAYAQFLAGMAFNNASLGYVHAMAHQLGGYY
NLP

HGVCNAVLLPIIVLAYNASVVAGRLKDVGVAMGLDIANLGDKEGAEATIQAVRDLAAS
I

GIPANLTELGAKKEDVPLLADHALKDACALTNPRQGDQKEVEELFLSAF"
BASE COUNT    470 a    396 c    392 g    489 t
ORIGIN    DraI site.
```
   1 aaaggcaaaa tcggtaacca catctcaatt attaaacaat acttcataat aaaaagacaa
  61 cttttcata attgcataa gtcttgatgt aaaaaataca tatttagaaa gaacaagcag
 121 ccttgctcat caccgctgtc gcgagtagaa aaatctcggc tttcagaaaa agaggccgct
 181 tcgttaaaca gactataaat gtgctggaat aaagcgaacc ccttgatctg ataaaactga
 241 tagacatatt gcttttgcgc tgcccgattg ctgaaaatgc gtaaaaggtg attttactcg
 301 ttttcaggaa aaactttgag aaaacgtctc gaaaacggga ttaaaacgca aaacaatag
 361 aaagcgattt cgcgaaaatg gttgttttcg ggttgttgct ttaaactagt atgtagggtg
 421 aggttatagc tatggcttct tcaactttt atattccttt cgtcaacgaa atgggcgaag
 481 gttcgcttga aaaagcaatc aaggatctta acggcagcgg ctttaaaaat gcgctgatcg
 541 tttctgatgc tttcatgaac aaatccggtg ttgtgaagca ggttgctgac ctgttgaaag
 601 cacagggtat taattctgct gtttatgatg gcgttatgcc gaacccgact gttaccgcag
 661 ttctggaagg ccttaagatc ctgaaggata acaattcaga cttcgtcatc tccctcggtg
 721 gtggttctcc ccatgactgc gccaaagcca tcgctctggt cgcaaccaat ggtggtgaag
 781 tcaaagacta cgaaggtatc gacaaatcta agaaacctgc cctgccttg atgtcaatca
 841 acacgacggc tggtacggct tctgaaatga cgcgtttctg catcatcact gatgaagtcc
 901 gtcacgttaa gatggccatt gttgaccgtc acgttacccc gatggtttcc gtcaacgatc
 961 ctctgttgat ggttggtatg ccaaaaggcc tgaccgccgc caccggtatg gatgctctga
1021 cccacgcatt tgaagcttat tcttcaacgg cagctactcc gatcaccgat gcttgcgcct
1081 tgaaggctgc gtccatgatc gctaagaatc tgaagaccgc ttcgacaac ggtaaggata
1141 tgccagctcg tgaagctatg gcttatgccc aattcctcgc tggtatggcc ttcaacaacg
1201 cttcgcttgg ttatgtccat gctatggctc accagttggg cggctactac aacctgccgc
1261 atggtgtctg caacgctgtt ctgcttccgc atgttctggc ttataacgcc tctgtcgttg
1321 ctggtcgtct gaaagacgtt ggtgttgcta tgggtctcga tatcgccaat ctcggtgata
1381 aagaaggcgc agaagccacc attcaggctg ttcgcgatct ggctgcttcc attggtattc
1441 cagcaaatct gaccgagctg ggtgctaaga agaagatgt gccgcttctt gctgaccacg
1501 ctctgaaaga tgcttgtgct ctgaccaacc cgcgtcaggg tgatcagaaa gaagttgaag
1561 aactcttcct gagcgctttc taatttcaaa acaggaaaac ggttttccgt cctgtcttga
1621 ttttcaagca aacaatgcct ccgatttcta atcggaggca tttgttttg tttattgcaa
1681 aaacaaaaaa tattgttaca aatttttaca ggctattaag cctaccgtca taaataattt
1741 gccattt
```
//
</PRE>

FIG. 11 (1)

```
LOCUS       SYNINCALAC   7922 bp   DNA   circular SYN      13-MAY-1996
DEFINITION  Cloning vector pNO3097 (incA) gene, partial cds; (stbA and stbB)
            complete cds; beta-lactamase complete cds; lac repressor complete
            cds; ORF repA4; lambda repressor complete cds.
ACCESSION   L05669
NID         g208643
KEYWORDS    beta-lactamase; incA gene; lac repressor; lambda repressor.
SOURCE      Cloning vector pNO3097 DNA.
  ORGANISM  Cloning vector pNO3097
            Synthetic sequences; Cloning vehicles.
REFERENCE   1  (bases 1 to 7922)
  AUTHORS   Dunn,J.J. and Studier,F.W.
  TITLE     Nucleotide sequence from the genetic left end of bacteriophage T7
            DNA to the beginning of gene 4
  JOURNAL   J. Mol. Biol. 148 (4), 303-330 (1981)
  MEDLINE   82078034
REFERENCE   2  (bases 1 to 7922)
  AUTHORS   Ryder,T.B., Davidson,D.B., Rosen,J.I., Ohtsubo,E. and Ohtsubo,H.
  TITLE     Analysis of plasmid genome evolution based on nucleotide-sequence
            comparison of two related plasmids of Escherichia coli
  JOURNAL   Gene 17 (3), 299-310 (1982)
  MEDLINE   82202792
REFERENCE   3  (bases 1 to 7922)
  AUTHORS   Sanger,F., Coulson,A.R., Hong,G.F., Hill,D.F. and Petersen,G.B.
  TITLE     Nucleotide sequence of bacteriophage lambda DNA
  JOURNAL   J. Mol. Biol. 162 (4), 729-773 (1982)
  MEDLINE   83189071
REFERENCE   4  (bases 1 to 7922)
  AUTHORS   Masai,H., Kaziro,Y. and Arai,K.
  TITLE     Definition of oriR, the minimum DNA segment essential for
            initiation of R1 plasmid replication in vitro
  JOURNAL   Proc. Natl. Acad. Sci. U.S.A. 80 (22), 6814-6818 (1983)
  MEDLINE   84070720
REFERENCE   5  (bases 1 to 7922)
  AUTHORS   Larsen,J.E., Gerdes,K., Light,J. and Molin,S.
  TITLE     Low-copy-number plasmid-cloning vectors amplifiable by derepression
            of an inserted foreign promoter
  JOURNAL   Gene 28 (1), 45-54 (1984)
  MEDLINE   84237559
REFERENCE   6  (bases 1 to 7922)
  AUTHORS   Yanisch-Perron,C., Vieira,J. and Messing,J.
  TITLE     Improved M13 phage cloning vectors and host strains: nucleotide
            sequences of the M13mp18 and pUC19 vectors
  JOURNAL   Gene 33 (1), 103-119 (1985)
  MEDLINE   85180545
```

FIG. 11 (2)

REFERENCE 7 (bases 1 to 7922)
  AUTHORS  Valentin-Hansen,P., Albrechtsen,B. and Love Larsen,J.E.
  TITLE    DNA-protein recognition: demonstration of three genetically
           separated operator elements that are required for repression of the
           Escherichia coli deoCABD promoters by the DeoR repressor
  JOURNAL  EMBO J. 5 (8), 2015-2021 (1986)
  MEDLINE  87004572
REFERENCE 8 (bases 1 to 7922)
  AUTHORS  Gerdes,K. and Molin,S.
  TITLE    Partitioning of plasmid R1. Structural and functional analysis of
           the parA locus
  JOURNAL  J. Mol. Biol. 190 (3), 269-279 (1986)
  MEDLINE  87060986
REFERENCE 9 (bases 1 to 7922)
  AUTHORS  Hu,M.C. and Davidson,N.
  TITLE    The inducible lac operator-repressor system is functional in
           mammalian cells
  JOURNAL  Cell 48 (4), 555-566 (1987)
  MEDLINE  87131068
REFERENCE 10 (bases 1 to 7922)
  AUTHORS  Tabuchi,A., Min,Y.N., Kim,C.K., Fan,Y.L., Womble,D.D. and
           Rownd,R.H.
  TITLE    Genetic organization and nucleotide sequence of the stability locus
           of IncFII plasmid NR1
  JOURNAL  J. Mol. Biol. 202 (3), 511-525 (1988)
  MEDLINE  89011976
REFERENCE 11 (bases 1 to 7922)
  AUTHORS  Womble,D.D. and Rownd,R.H.
  TITLE    Genetic and physical map of plasmid NR1: comparison with other
           IncFII antibiotic resistance plasmids
  JOURNAL  Microbiol. Rev. 52 (4), 433-451 (1988)
  MEDLINE  89181346
REFERENCE 12 (bases 1 to 7922)
  AUTHORS  Rose,R.E.
  TITLE    The nucleotide sequence of pACYC177
  JOURNAL  Nucleic Acids Res. 16 (1), 356 (1988)
  MEDLINE  88124215
REFERENCE 13 (bases 1 to 7922)
  AUTHORS  Masai,H. and Arai,K.
  TITLE    RepA protein- and oriR-dependent initiation of R1 plasmid
           replication: identification of a rho-dependent transcription
           terminator required for cis-action of repA protein
  JOURNAL  Nucleic Acids Res. 16 (14A), 6493-6514 (1988)
  MEDLINE  88289416
REFERENCE 14 (bases 1 to 7922)
  AUTHORS  Masai,H. and Arai,K.

FIG. 11 (3)

```
     TITLE     Leading strand synthesis of R1 plasmid replication in vitro is
               primed by primase alone at a specific site downstream of oriR
     JOURNAL   J. Biol. Chem. 264 (14), 8082-8090 (1989)
     MEDLINE   89255240
REFERENCE   15 (bases 1 to 7922)
     AUTHORS   Blomberg,P., Nordstrom,K. and Wagner,E.G.
     TITLE     Replication control of plasmid R1: RepA synthesis is regulated by
               CopA RNA through inhibition of leader peptide translation
     JOURNAL   EMBO J. 11 (7), 2675-2683 (1992)
     MEDLINE   92331620
REFERENCE   16 (bases 1 to 7922)
     AUTHORS   Keener,J. and Nomura,M.
     TITLE     Dominant lethal phenotype of a mutation in the -35 recognition
               region of E. coli sigma 70
     JOURNAL   Unpublished (1993)
FEATURES             Location/Qualifiers
     source          1..7922
                     /organism="Cloning vector pNO3097"
     misc_feature    1..1722
                     /note="NaeI-TaqI fragment from pJEL126 carrying the parA
                     partitioning locus of R1. This corresponds to positions
                     -28 to 1693 of ref. 4."
                     /citation=[7]
                     /citation=[10]
                     /citation=[8]
     misc_feature    1..7922
                     /note="plasmid copy number can be greatly amplified by
                     incubation at 42 degrees, which inactivates lambda
                     repressor and causes increased expression of the
                     replication protein; pNO3097 is a low copy cloning vector
                     with an R1 origin and partitioning system, amp resistance,
                     lac repressor and a polylinker downstream of the lac
                     promoter"
                     /citation=[16]
                     /citation=[5]
     gene            complement(106..168)
                     /gene="incA"
     CDS             complement(106..168)
                     /gene="incA"
                     /note="cis-acting incompatibility locus required for
                     stable maintenance of the plasmid"
                     /citation=[10]
                     /citation=[8]
                     /codon_start=1
                     /db_xref="PID:g940308"
                     /translation="MFWVLSGFVCQVYPISTINQ"
```

FIG. 11 (4)

```
-35_signal    109..114
              /gene="incA"
-10_signal    131..136
              /gene="incA"
gene          211..1173
              /gene="stbA"
CDS           211..1173
              /gene="stbA"
              /note="StbA and StbB are both required for stable
              maintenance of the plasmid"
              /citation=[10]
              /citation=[8]
              /codon_start=1
              /db_xref="PID:g208644"
```

/translation="MLVFIDDGSTNIKLQWQESDGTIKQHISPNSFKREWAVPFGDKK

VFNYTLNGEQYSFDPTSPDAVVTTNIAWQYSDVNVVAVHHALLTSGLPVSEVDIVCTL

PLTEYYDRNNQPNTENIERKKANFRKKITLNGGDTFTIKDVKVMPESIPAGYEVLQEL

DELDSLLIIDLGGTTLDISQVMGKLSGISKIYGDSSLGVSLVTSAVKDALSLARTKGS

SYLADDIIIHRKDNNYLKQRINDENKISIVTEAMNEALRKLEQRVLNTLNEFSGYTHV
    MVIGGGAELICDAVKKHTQIRDERFFKTNNSQYDLVNGMYLIGN"

```
gene          1173..1631
              /gene="stbB"
CDS           1173..1631
              /gene="stbB"
              /note="one base was omitted in the sequence of ref.3
              resulting in a shorter reading frame, but was corrected in
              Genbank accessno. X04268 to agree with ref. 4"
              /citation=[10]
              /citation=[8]
              /codon_start=1
              /db_xref="PID:g208645"
```

/translation="MMDKRRTIAFKLNPDVNQTDKIVCDTLDSIPQGERSRLNRAALT

AGLALYRQDPRTPFLLCELLTKETTFSDIVNILRSLFPKEMADFNSSIVTQSSSQQEQ
    KSDEETKKNATKLIKLIQLLLSSLYPLSGWIKGTQSSYFLTSHYIIVIMK"

```
misc_feature  1723..2755
              /note="AatII-DraI fragment of pACYC 177 carrying the bla
              gene, positions 3567 to 659 of ref. 5, identical to pBR322
              sequence"
              /citation=[12]
```

FIG. 11 (5)

CDS        1854..2714
           /note="25 micrograms/ml ampicillin does not inhibit
           growth, but 50 micrograms/ml causes some growth
           inhibition"
           /citation=[12]
           /codon_start=1
           /product="beta-lactamase"
           /db_xref="PID:g208646"

/translation="MSIQHFRVALIPFFAAFCLPVFAHPETLVKVKDAEDQLGARVGY

IELDLNSGKILESFRPEERFPMMSTFKVLLCGAVLSRVDAGQEQLGRRIHYSQNDLVE

YSPVTEKHLTDGMTVRELCSAAITMSDNTAANLLLTTIGGPKELTAFLHNMGDHVTRL

DRWEPELNEAIPNDERDTTMPAAMATTLRKLLTGELLTLASRQQLIDWMEADKVAGPL

LRSALPAGWFIADKSGAGERGSRGIIAALGPDGKPSRIVVIYTTGSQATMDERNRQIA
           EIGASLIKHW"
    misc_feature   2756..3903
           /note="lac DNA from position 48 of Genbank file ecolac (31
           bp upstream of start codon) to position 1179 (18bp
           downstream of stop codon); HindIII-SalI fragment of pRSV1
           carrying the gene for lac repressor flanked by linker DNA.
           EcoRI sites have been filled in"
           /citation=[9]
    CDS        2801..3883
           /note="start codon was changed from GTG to ATG, in this
           construction, the lacrepressor gene is cotranscribed with
           the gene for beta-lactamase"
           /citation=[9]
           /codon_start=1
           /product="lac repressor"
           /db_xref="PID:g208647"

/translation="MKPVTLYDVAEYAGVSYQTVSRVVNQASHVSAKTREKVEAAMAE

LNYIPNRVAQQLAGKQSLLIGVATSSLALHAPSQIVAAIKSRADQLGASVVVSMVERS

GVEACKAAVHNLLAQRVSGLIINYPLDDQDAIAVEAACTNVPALFLDVSDQTPINSII

FSHEDGTRLGVEHLVALGHQQIALLAGPLSSVSARLRLAGWHKYLTRNQIQPIAEREG

DWSAMSGFQQTMQMLNEGIVPTAMLVANDQMALGAMRAITESGLRVGADISVVGYD
DT

FIG. 11 (6)

```
         EDSSCYIPPSTTIKQDFRLLGQTSVDRLLQLSQGQAVKGNQLLPVSLVKRKTTLAPNT
              QTASPRALADSLMQLARQVSRLESGQ"
     misc_feature   3904..4100
                    /note="DraI-BstBI fragment of pACYC177, from position 660
                    to position 855 of ref. 5, included because of the method
                    of construction, no known function"
                    /citation=[12]
     misc_RNA       complement(4097)
                    /note="5' end of RNA III inferred from known promoter
                    within the R1 fragment"
                    /citation=[2]
     misc_feature   4101..7454
                    /note="NdeI-Eco47III fragment of pJEL126 carrying a fusion
                    of the lambda Pr promoter to the replication genes of R1,
                    controlled by heat sensitive lambda repressor"
                    /citation=[7]
                    /citation=[5]
     misc_feature   4101..6408
                    /note="NdeI-BlgII fragmewnt of R1 extending from position
                    2058 to position-258 of ref. 7, including the origin and
                    genes for replication and copy number control"
                    /citation=[2]
     CDS            complement(4159..4545)
                    /note="ORF repA4"
                    /citation=[2]
                    /citation=[11]
                    /codon_start=1
                    /db_xref="PID:g208648"
                    /translation="MHLPPQAAGPDRSHFSYNTQKQPPEKPRSSAEPKPQSPSLITEK RPRPGPKGRNRVAFNYECCNYIFIAVSLLAGSSQYTLVSGPHGPLTRRHAPTSGKPSS
              GPLPPRTEALSWLKAGMVWQGWGWVR"
     misc_feature   4181
                    /note="site of initiation for leading strand DNA
                    synthesis"
                    /citation=[14]
     rep_origin     4518..4735
                    /standard_name="oriR"
                    /citation=[4]
                    /direction=left
     misc_feature   complement(4736..4906)
                    /standard_name="CIS"
                    /note="the CIS sequence is required for cis-activation of
                    oriR by the RepA protein"
                    /citation=[13]
```

FIG. 11 (7)

```
gene        complement(4908..5765)
            /gene="repA"
CDS         complement(4908..5765)
            /gene="repA"
            /note="RepA protein activates initiation of DNA
            replication at oriR, preferentially acting in cis.
            Synthesis of RepA is translationally coupled to that of
            tap"
            /citation=[15]
            /citation=[2]
            /codon_start=1
            /db_xref="PID:g208649"
            /transl_table=11
```

/translation="MTDLHQTYYRQVKNPNPVFTPREGAGTPKFREKPMEKAVGLTSR

FDFAIHVAHARSRGLRRRMPPVLRRRAIDALLQGLCFHYDPLANRVQCSITTLAIECG

LATESGAGKLSITRATRALTFLSELGLITYQTEYDPLIGCYIPTDITFTLALFAALDV

SEDAVAAARRSRVEWENKQRKKQGLDTLGMDELIAKAWRFVRERFRSYQTELQSRGIK

RARARRDANRERQDIVTLVKRQLTREISEGRFTANGEAVKREVERRVKERMILSRNRN
            YSRLATASP"

```
gene        complement(5762..5832)
            /gene="tap"
CDS         complement(5762..5832)
            /partial
            /gene="tap"
            /note="translation of tap is required for translation of
            repA protein"
            /citation=[15]
            /codon_start=1
            /db_xref="PID:g554559"
            /translation="MPGKVQDFFLCSLLLRIVSAGWC"
misc_RNA    5850..5940
            /standard_name="CopA"
            /note="CopA inhibits translation of tap, thus ultimately
            inhibiting expression of the RepA protein and initiation
            of plasmid replication"
            /citation=[15]
misc_RNA    complement(6016)
            /note="5' end of RNA II, which extends leftward, encodes
            tap and RepA proteins, and mostly terminates in the CIS
            region"
            /citation=[13]
```

FIG. 11 (8)

```
                    /citation=[2]
      misc_feature  complement(6057..6321)
                    /standard_name="CopB"
                    /note="CopB regulates RNA II synthesis, in this plasmid it
                    has been frameshifted by filling in the BglII site at
                    6160, so copy number is expected to increase to about 5"
                    /citation=[2]
                    /citation=[5]
      misc_feature  6409..7454
                    /note="BglII-Eco47III fragment of lambda including the Pr
                    promoter and the cI857 allele of lambda repressor
                    extending from position 38,105 to 37,060 of ref. 13"
                    /citation=[3]
      -10_signal    complement(6498..6503)
      protein_bind  6500..6516
                    /citation=[3]
                    /bound_moiety="lambda repressor"
      misc_RNA      complement(6501)
                    /note="5' end of the transcript from the powerful lambda
                    Pr promoter, encodes RepA protein, regulated by
                    heat-sensitive lambda repressor"
                    /citation=[3]
                    /citation=[5]
      -35_signal    complement(6521..6526)
      protein_bind  6524..6540
                    /citation=[3]
                    /bound_moiety="lambda repressor"
      protein_bind  6547..6563
                    /citation=[3]
                    /bound_moiety="lambda repressor"
      CDS           6574..7287
                    /note="cI857 heat-sensitive allele of lambda repressor,
                    shift to 42 causes inactivation of repressor, release of
                    repression of the Pr promoter, and high expression of RepA
                    protein"
                    /citation=[3]
                    /citation=[5]
                    /codon_start=1
                    /product="lambda repressor"
                    /db_xref="PID:g208651"
```

/translation="MSTKKKPLTQEQLEDARRLKAIYEKKKNELGLSQESVADKMGMG

QSGVGALFNGINALNAYNAALLTKILKVSVEEFSPSIAREIYEMYEAVSMQPSLRSEY

EYPVFSHVQAGMFSPKLRTFTKGDAERWVSTTKKASDSAFWLEVEGNSMTAPTGSKPS

FIG. 11 (9)

FPDGMLILVDPEQAVEPGDFCIARLGGDEFTFKKLIRDSGQVFLQPLNPQYPMIPCNE
SCSVVGKVIASQWPEETFG"
  misc_feature    7455..7727
              /note="SpeI-RsaI fragment from position 7697 to 7425 in
              ref. 15 of phage T7. Contains the early transcriptional
              terminator"
              /citation=[1]
  stem_loop      complement(7572..7591)
              /note="early transcriptional terminator from phage T7,
              transcripts from the lac promoter and the polylinker
              region would terminate around position 7570"
              /citation=[1]
  misc_feature    7728..7754
              /note="EcoRI-XbaI fragment of the pUC19 polylinker,
              positons 397 to 423 of ref. 16, KpnI is a unique site"
              /citation=[6]
  misc_feature    7755..7790
              /note="custom polylinker provides unique sites for XbaI,
              XhoI, StuI, NdeI, PmlI, and EcoRI located downstream of
              the lac promoter"
  misc_feature    7791..7914
              /note="EcoRI-AseI fragment from pUC18 contains the
              wild-type lac promoter and the lac operator, positons 1298
              to 1174 of the Genbank file ecolac, features listed below
              are from ecolac"
              /citation=[6]
  protein_bind    7823..7840
              /note="transcription from the lac promoter is regulated by
              binding of lac repressor to the lac operator, addition of
              inducer (IPTG) prevents repressor binding"
              /bound_moiety="lac repressor"
  misc_RNA       complement(7842)
              /note="5' end of lac mRNA, transcribed leftward into the
              polylinker"
  -10_signal     complement(7849..7854)
  -35_signal     complement(7873..7878)
  protein_bind    7896..7911
              /note="the complex of cAMP and the CRP protein activates
              transcription of the lac promoter by binding to this site,
              growth in glucose gives low cAMP levels thus very low lac
              expression"
              /bound_moiety="cAMP receptor protein (CRP)"
  misc_feature    7915..7922
              /note="XbaI-HincII fragment of the pUC19 polylinker,
              positions 424 to 431 of ref. 16"

FIG.11(10)

/citation=[6]
BASE COUNT    2161 a   1843 c   1908 g   2010 t
ORIGIN
   1 ggcggagtaa aaagaggagc ccggcgtcat cttttgttac ccgccaaaca aaacccaaaa
  61 acaacccata cccaacccaa taaaacacca aaacaagaca aataatcatt gattgatggt
 121 tgaaatgggg taaacttgac aaacaaaccc acttaaaacc caaaacatac ccaaacacac
 181 accaaaaaaa caccataagg agttttataa atgttggtat tcattgatga cggttcaaca
 241 aacatcaaac tacagtggca ggaaagcgac ggaacaatta aacagcacat tagcccgaac
 301 agcttcaaac gcgagtgggc agtcccttt ggtgataaaa aggtctttaa ctacacactg
 361 aacggcgaac agtattcatt tgatccaacc agcccggatg ctgtagtcac aaccaatatc
 421 gcatggcaat acagcgacgt taatgtcgtt gcagtgcatc acgccttact gaccagtggt
 481 ctgccggtaa gcgaagtgga tattgtttgc acacttcctc tgacagagta ttacgacaga
 541 aataaccaac ccaatacgga aaatattgag cgtaagaaag caaacttccg gaaaaaaatt
 601 acattaaatg gcggggatac attcacaata aaagatgtaa aagtcatgcc tgaatctata
 661 ccggcaggtt atgaagttct acaagaactg gatgagttag attctttatt aattatagat
 721 ctcgggggca ccacattaga tattctcag gtaatgggga aattatcggg gatcagtaaa
 781 atatacggag actcatctct tggtgtctct ctggttacat ctgcagtaaa agatgccctt
 841 tctcttgcga gaacaaaagg aagtagctat cttgctgacg atataatcat tcacagaaaa
 901 gataataact atctgaagca acgaattaat gatgagaaca aaatatcaat agtcaccgaa
 961 gcaatgaatg aagcacttcg taaacttgag caacgtgtat taaatacgct caatgaattt
1021 tctggttata ctcatgttat ggttataggc ggtggcgcag aattaatatg cgatgcagta
1081 aaaaaacaca cacagattcg tgatgaacgt tttttcaaaa ccaataactc tcaatatgat
1141 ttagttaacg gtatgtatct cataggtaat taatgatgga caagcgcaga accattgcct
1201 tcaaactaaa tccagatgta aatcaaacag ataaaattgt ttgtgataca ctggacagta
1261 tcccgcaagg ggaacgaagc cgccttaacc gggccgcact gacggcaggt ctggccttat
1321 acagacaaga tccccggacc cctttccttt tatgtgagct gctgacgaaa gaaaccacat
1381 tttcagatat cgtgaatata ttgagatcgc tatttccaaa agagatggcc gattttaatt
1441 cttcaatagt cactcaatcc tcttcacaac aagagcaaaa aagtgatgaa gagaccaaaa
1501 aaaatgcgac gaagctaata aaattaattc aattattatt gagttcccct tatccactat
1561 caggctggat aaagggaact caatcaagtt attttcttac cagtcattac ataatcgtta
1621 ttatgaaaata atcgtttgca ctgtctctgt tattcaggca atttcaataa aggcacttgc
1681 tcacgctctg tcattttctg aaactcttca tgctgcattt cgcaggtggc acttttcggg
1741 gaaatgtgcg cggaacccct atttgtttat ttttctaaat acattcaaat atgtatccgc
1801 tcatgagaca ataaccctga taaatgcttc aataatattg aaaaaggaag agtatgagta
1861 ttcaacattt ccgtgtcgcc cttattccct ttttgcggc attttgcctt cctgtttttg
1921 ctcacccaga aacgctggtg aaagtaaaag atgctgaaga tcagttgggt gcacgagtgg
1981 gttacatcga actggatctc aacagcggta agatccttga gagttttcgc cccgaagaac
2041 gttttccaat gatgagcact tttaaagttc tgctatgtgg cgcggtatta tcccgtgttg
2101 acgccgggca agagcaactc ggtcgccgca tacactattc tcagaatgac ttggttgagt
2161 actcaccagt cacagaaaag catcttacgg atggcatgac agtaagagaa ttatgcagtg
2221 ctgccataac catgagtgat aacactgcgg ccaacttact tctgacaacg atcggaggac
2281 cgaaggagct aaccgctttt ttgcacaaca tgggggatca tgtaactcgc cttgatcgtt
2341 gggaaccgga gctgaatgaa gccataccaa acgacgagcg tgacaccacg atgcctgcag
2401 caatggcaac aacgttgcgc aaactattaa ctggcgaact acttactcta gcttcccggc
2461 aacaattaat agactggatg gaggcggata aagttgcagg accacttctg cgctcggccc
2521 ttccggctgg ctggtttatt gctgataaat ctggagccgg tgagcgtggg tctcgcggta

FIG.11(11)

```
2581 tcattgcagc actggggcca gatggtaagc cctcccgtat cgtagttatc tacacgacgg
2641 ggagtcaggc aactatggat gaacgaaata gacagatcgc tgagataggt gcctcactga
2701 ttaagcattg gtaactgtca gaccaagttt actcatatat actttagatt gatttagctt
2761 gaattaattc ccggaagaga gtcaattcag ggtggtgaat atgaaaccag taacgttata
2821 cgatgtcgca gagtatgccg gtgtctctta tcagaccgtt tcccgcgtgg tgaaccaggc
2881 cagccacgtt tctgcgaaaa cgcgggaaaa agtggaagcg gcgatggcgg agctgaatta
2941 cattcccaac cgcgtggcac aacaactggc gggcaaacag tcgttgctga ttggcgttgc
3001 cacctccagt ctggccctgc acgcgccgtc gcaaattgtc gcggcgatta aatctcgcgc
3061 cgatcaactg ggtgccagcg tggtggtgtc gatggtagaa cgaagcggcg tcgaagcctg
3121 taaagcggcg gtgcacaatc ttctcgcgca acgcgtcagt gggctgatca ttaactatcc
3181 gctggatgac caggatgcca ttgctgtgga agctgcctgc actaatgttc cggcgttatt
3241 tcttgatgtc tctgaccaga cacccatcaa cagtattatt ttctcccatg aagacggtac
3301 gcgactgggc gtggagcatc tggtcgcatt gggtcaccag caaatcgcgc tgttagcggg
3361 cccattaagt tctgtctcgg cgcgtctgcg tctggctggc tggcataaat atctcactcg
3421 caatcaaatt cagccgatag cggaacggga aggcgactgg agtgccatgt ccggttttca
3481 acaaaccatg caaatgctga atgagggcat cgttcccact gcgatgctgg ttgccaacga
3541 tcagatggcg ctgggcgcaa tgcgcgccat taccgagtcc gggctgcgcg ttggtgcgga
3601 tatctcggta gtgggatacg acgataccga agacagctca tgttatatcc cgccgtcaac
3661 caccatcaaa caggattttc gcctgctggg gcaaaccagc gtggaccgct tgctgcaact
3721 ctctcagggc caggcggtga agggcaatca gctgttgccc gtctcactgg tgaaaagaaa
3781 aaccaccctg gcgcccaata cgcaaaccgc ctctccccgc gcgttggccg attcattaat
3841 gcagctggca cgacaggttt cccgactgga aagcgggcag tgagcgcaac gcaattaatg
3901 tcgaaaaact tcattttaa tttaaaagga tctaggtgaa gatcctttt gataatctca
3961 tgaccaaaat cccttaacgt gagttttcgt tccactgagc gtcagacccc gtaataagat
4021 gatcttcttg agatcgtttt ggtctgcgcg taatctcttg ctctgaaaac gaaaaaaccg
4081 ccttgcaggg cggttttcg tatgatacag gagtaaaacc gccgaagccc ggcgtaagcc
4141 ggtactgatt gatagatttc accttaccca tccccagccc tgccagacca tacccgcttt
4201 cagccatgag agagcttctg tgcgcggtcg gagtggtccc gacgagggtt tacccgaagt
4261 cggggcgtgt ctccgcgtta gcgggccgtg agggccgctt acgagcgtgt actgagaact
4321 tccagcgaga agactgacag cgatgaagat gtagttacaa cattcataat taaaagcgac
4381 tctgttccgg ccctttgggc cggggcgggg ccgcttttca gttatgaggg aggggctttg
4441 tggtttcggt tctgcgctgg accggggttt ttctggaggt tgttttgtg tgttgtaact
4501 aaagtggctc cggtcggggc ccgccgcttg cggtgggagg tgcatatctg tctgtccaca
4561 ggacaggcag tgaataggtt ttcttttaa atgaatgtaa ttaagtagtt taaggagat
4621 ataaacaggt gtttaaaaga tacattgcac cctgtaagac tggcggctgg cgcttttatga
4681 catgaacggt tgtaaccta tggggaagtc ccttgcagtt aaatgtggat aagcaaaatt
4741 ccccgtcgct gaggcgtatt ttgtattaaa aacaggggga atcggatgct ccagaaggtg
4801 gatgatgaga ttgttttttg catgcgacgc tgttttttg tgcaccggcg ggcttcaggc
4861 gtgcggatgc ctccggcgca ggccggatta ttctgaggag atcactttca gggagaagct
4921 gtggccagcc ggctgtaatt gcggttacgt gacagaatca tgcgctcctt cacacgacgc
4981 tccacttcgc gttttaccgc ctcaccatta gcagtgaagc gtccttccga gatttcacgc
5041 gtcagctgcc gtttcactag ggtgacgata tcctgacgtt ctctgttcgc atcacgacgc
5101 gcacgggcac gtttattcc acgggactga agctctgtct ggtaactgcg gaaacgctca
5161 cgcacaaaac gccaggcttt cgctatcagc tcatccatac ccagggtatc cagccctgc
5221 tttttgcgct gtttgttttc ccattcaaca cgactgcggc gcgcagctgc cactgcatcc
5281 tcagacacat caagggcagc aaacagagcc agtgtgaacg tgatgtcggt cggaatgtag
```

FIG. 11 (12)

```
5341 cacccgataa gcgggtcata ttccgtctgg taggtaatca gtcccagctc tgacaggaac
5401 gtcagggccc gggtggcacg ggtgatggag agttttcctg caccggactc tgtcgccagt
5461 ccgcactcaa tggccagtgt ggtgatggaa cactggacgc ggttggccag cgggtcatag
5521 tggaaacaca gcccctgcag cagcgcatca atagcccgtc gacgcagcac cggtggcatg
5581 cgccgacgca gaccacggga acgggcatgc gccacatgaa tggcgaaatc aaaacgggag
5641 gtgaggccca ccgccttttc catcggtttt tcgcggaact tcggcgttcc ggcaccttca
5701 cggggagtga acaccggatt cgggttcttt acctggcggt aatacgtttg gtgaagatca
5761 gtcacaccat cctgcactta caatgcgcag aaggagcgag cacagaaaga agtcttgaac
5821 ttttccgggc atataactat actccccgca tagctgaatt gttggctata cggtttaagt
5881 gggccccggt aatcttttcg tactcgccaa agttgaagaa gattatcggg gttttgctt
5941 ttctggctcc tgtaaatcca catcagaacc agttccttgc caccttacgg cgtggcagcc
6001 acaaaattcc ttaaacgatc agtaatctag ctagctacgc cacaaagtaa agtcttttac
6061 tttagtatat ccagtctctg cagttcatct ttgatgattt tctcaacgaa ctgagcctgt
6121 gttatcccct ctctctcgca gtactcaacc atgagatcga tctttcagag gatttttgac
6181 aaaaacttt atctctttgt gtgtaagacg ttttcttgca acagcggcca tttgttctc
6241 agagtcagtc ataggcttac ctctgcgcac aaaccgcttt tgactcaatg aggaagtcac
6301 tgcattttct gtctgcgaca tctcgcctcc tcaatactca aacagggatc gtttcgcaga
6361 ggatactaca gtttttgaa atcagcaact tgagaattgt gacgaagatc tttagctgtc
6421 ttggtttgcc caaagcgcat tgcataatct ttcagggtta tgcgttgttc catacaacct
6481 ccttagtaca tgcaaccatt atcaccgcca gaggtaaaat agtcaacacg cacggtgtta
6541 gatatttatc ccttgcggtg atagatttaa cgtatgagca caaaaaagaa accattaaca
6601 caagagcagc ttgaggacgc acgtcgcctt aaagcaattt atgaaaaaaa gaaaaatgaa
6661 cttggcttat cccaggaatc tgtcgcagac aagatgggga tggggcagtc aggcgttggt
6721 gctttattta atggcatcaa tgcattaaat gcttataacg ccgcattgct tacaaaaatt
6781 ctcaaagtta gcgttgaaga atttagccct tcaatcgcca gagaaatcta cgagatgtat
6841 gaagcggtta gtatgcagcc gtcacttaga agtgagtatg agtaccctgt tttttctcat
6901 gttcaggcag ggatgttctc acctaagctt agaaccttta ccaaaggtga tgcggagaga
6961 tgggtaagca caaccaaaaa agccagtgat tctgcattct ggcttgaggt tgaaggtaat
7021 tccatgaccg caccaacagg ctccaagcca agctttcctg acggaatgtt aattctcgtt
7081 gaccctgagc aggctgttga gccaggtgat ttctgcatag ccagacttgg gggtgatgag
7141 tttaccttca agaaaactgat cagggatagc ggtcaggtgt tttacaacc actaaaccca
7201 cagtacccaa tgatcccatg caatgagagt tgttccgttg tgggaaagt tatcgctagt
7261 cagtggcctg aagagacgtt tggctgatcg gcaaggtgtt ctggtcggcg catagctgat
7321 aacaattgag caagaatctt catcgaatta ggggaatttt cactcccctc agaacataac
7381 atagtaaatg gattgaatta tgaagaatgc tttttatgcg acttaccgca gcaaaaataa
7441 agggaaagat aagcctagtg ctacttgagg gtataccgca agaatatacg caagcgtcag
7501 gatagctgcc aaagccgcaa ggaatttacc aaccttctta aacataaagt gtctccttat
7561 aaacgcagaa aggcccaccc gaaggtgagc cagtgtgatt acattttctc ttgagggttg
7621 tcctcggtgc cacggaacat tacgaacgat gggtgccgca aagagccatc aggtgtttcc
7681 tccatgtagc taatttgaca cgcccagcca tcgtaagggt taatagtaat tcgagctcgg
7741 tacccgggga tcctctagag ctcgaggcct catatggatc cacgtgaatt cgtaatcatg
7801 tcatagctgt ttcctgtgtg aaattgttat ccgctcacaa ttccacacaa catacgagcc
7861 ggaagcataa agtgtaaagc ctggggtgcc taatgagtga gctaactcac attactagag
7921 tc
```

US 6,306,639 B1

GENETICALLY MODIFIED CYANOBACTERIA FOR THE PRODUCTION OF ETHANOL, THE CONSTRUCTS AND METHOD THEREOF

This application is a continuation-in-part of Ser. No. 08/801,331, filed Feb. 19, 1997, now abandoned.

FIELD OF THE INVENTION

This invention relates to the genetic modification of Cyanobacteria for the production of ethanol. In particular, this invention relates to the genetic modification of Synechococcus by incorporating the genetic information encoding for pyruvate decarboxylase (pdc) and alcohol dehydrogenase (adh).

BACKGROUND

Ethanol is an energy source which is particularly attractive because it can be utilized with little waste. In addition, ethanol derived from living organisms is an attractive alternative to petroleum based fuels because it is a renewable resource.

A number of alternatives for the production of ethanol from living organisms have been investigated using microorganisms.

The production of ethanol by microorganisms has, in large part, been investigated using the yeast Saccharomyces and bacteria Zymomonas, which is a facultative anaerobic. Both of these microorganisms contain the genetic information to produce enzymes pdc and adh, which enzymes are used to produce ethanol from pyruvate, a product of the glycolytic pathway.

U.S. Pat. No. 4,242,455 to Muller et al. describes a continuous process in which an aqueous slurry of carbohydrate polymer particles, such as starch granules and/or cellulose chips, fibres, etc., are acidified with a strong inorganic acid to form a fermentable sugar. The fermentable sugar is then fermented to ethanol with at least two strains of Saccaromyces. U.S. Pat. No. 4,350,765 to Chibata et al. describes a method of producing ethanol in a high concentration by using an immobilized Saccharomyces or Zymomonas and a nutrient culture broth containing a fermentative sugar. U.S. Pat. No. 4,413,058 to Arcuri et al. describes a new strain of *Zymomonas mobilis* which is used to produce ethanol by placing the microorganism in a continuous reactor column and passing a stream of aqueous sugar through said column.

PCT Application WO/88/09379 to Hartley et al. describes the use of facultative anaerobic thermophilic bacteria strains which produce ethanol by fermenting a wide range of sugars, including cellobiose and pentoses. These bacteria strains contain a mutation in lactate dehydrogenase. As a result, these strains which would normally produce lactate under anaerobic conditions, produce ethanol instead.

In addition, *Escherichia coli* has been genetically altered to produce ethanol by inserting the genetic material encoding for the adh and pdc enzymes using the pLOI295 plasmid. The genetic material encoding the pdc enzyme was isolated from *Zymomonas mobilis*. This altered *Escherichia coli* produces ethanol; however, it still requires a variety of organic substrates for bacterial metabolism and growth. (Ingram, et al. (1987), "Genetic Engineering of Ethanol Production in *Escherichia coli*" (Appl. Environ Microbiol. 53: 2420–2425)

All of the above prior art describe microorganisms which utilize a carbohydrate/sugar substrate to produce ethanol. As such, these processes are costly because a feed substrate of carbohydrates/sugars is required in order for the microorganisms to be able to produce ethanol. Hence, the cost of these systems is a deterrent to the refinement and scale up of such systems for the production of ethanol.

It is highly desirable to find a microorganism which can effectively produce ethanol wherein said microorganism requires minimal feed substrate.

SUMMARY OF THE PRESENT INVENTION

In an aspect of the present invention, there is provided genetically modified photosynthetic Cyanobacteria which are capable of producing ethanol. The Cyanobacteria are genetically modified by the insertion of DNA fragments encoding the enzymes pdc and adh. Consequently, the enzymes pdc and adh are produced in vivo by the genetically modified Cyanobacteria; which enzymes convert pyruvate to acetaldehyde and acetaldehyde to ethanol, respectively. In particular, Synechococcus is a preferred Cyanobacteria of the present invention. In a preferred embodiment, transformed Synechococcus produce ethanol in recoverable quantities of at least 1.7 $\mu$mol of ethanol per mg of chlorophyll per hour.

In a further aspect of the present invention, there is provided genetically modified Cyanobacteria which contain constructs comprising a temperature inducible gene so that the ethanol is produced only once a particular temperature is reached. In a particular embodiment, the construct comprises the CI857 temperature inducible gene. The CI857 temperature inducible gene maybe used in the form of the CI-PL promoter, EMBL Accessive No. L05669, SEQ. ID. No. 7.

In a further aspect of the present invention, there is provided genetically modified Cyanobacteria which contain constructs comprising DNA fragments encoding the pdc and adh enzymes obtained from the *Zymomonas mobilis* plasmid pLOI295.

In a further aspect of the present invention, the Cyanobacteria is Synechococcus PCC 7942 or other transformable strains capable of producing ethanol when a construct comprising DNA fragments encoding pdc and adh enzymes from the pLOI295 plasmid is transformed into the Synechococcus.

In a further aspect of the present invention, there is provided genetically modified Cyanobacteria containing constructs comprising DNA fragments from the *Zymomonas mobilis* plasmid pLOI295 encoding the pdc and adh enzymes wherein the DNA fragment encoding the pdc enzyme is listed in the European Molecular Biology Laboratories ("EMBL") as Accession No. M15393 and as described in Conway et al. (1987) J. Bacterial 169: 949–954 SEQ. ID. No. 5, or a gene sequence that encodes the pdc enzyme and is capable of expression in Cyanobacteria.

In a further aspect of the present invention, there is provided genetically modified Cyanobacteria containing constructs comprising DNA fragments from the *Zymomonas mobilis* plasmid pLOI295 encoding the pdc and adh enzymes wherein the DNA fragment encoding the adh enzyme is adh II listed in the EMBL as Accession No. M15394 and as described in Conway et al. (1987) J. Bacterial 169: 2591–2597, SEQ. ID. No. 6 or a gene sequence that encodes the adh enzyme and that is capable of expression in Cyanobacteria.

In another aspect of the present invention there is provided a genetically modified Cyanobacteria capable of producing ethanol produced according to the following steps:

a. selecting an appropriate promoter;
b. ligating said promoter to pdc and adh encoding DNA sequence;
c. cloning said ligated promoter and said pdc and adh encoding DNA into an appropriate construct;
d. transforming the construct into the Cyanobacteria In a preferred embodiment the modified Cyanobacteria is a modified Synechococcus PCC 7942. Constructs produced according to these steps include constructs selected from the group consisting of pCB4-Rpa, pCB4-LRpa and pCB4-LR (TF)pa.

In a further aspect of the present invention, there is provided a construct comprising a promoter from Synechococcus operatively linked to genes encoding pdc and adh enzymes from the Zymomonas mobilis pLOI295 plasmid.

In a further aspect of the present invention there is provided a construct wherein the promoter comprises an rbcLS operon of Synechococcus. In another aspect the promoter further comprises a lacZ operon of Escherichia coli.

In a further aspect of the present invention there is provided a construct wherein the DNA fragments encoding the pdc and adh enzymes are listed in EMBL as Accession No. M15393 and M15394, SEQ. ID. Nos. 5 and 6, respectively, or analogous sequences thereof that include encoding for the pdc enzyme and the adh enzyme, respectively.

In a further aspect of the present invention, there is provided constructs encoding the pdc and adh enzymes wherein the constructs include a temperature inducible gene CI857.

In a further aspect of the invention, there is provided a promoter capable of being used in a construct encoding pdc and adh enzymes obtained from Zymomonas mobilis, wherein the promoter comprises a rbcLS operon of Synechococcus.

In a further aspect of the present invention, there is provided a promoter capable of being used in a construct encoding the pdc and adh enzymes obtained from Zymomonas mobilis, wherein the promoter comprises a rbcLS operon of Synechococcus and a lacZ operon of Escherichia coli.

In a further aspect of the present invention there is provided a CI-PL promoter which is temperature inducible and is capable of being used in a construct encoding pdc and adh enzymes obtained from Zymomonas mobilis wherein said promoter is activated only once a particular temperature is reached.

In a further aspect of the present invention there is provided a process for making genetically modified Cyanobacteria by incorporating a construct encoding the pdc and adh enzymes from the Zymomonas mobilis pL01295 plasmid, or other suitable source of pdc and adh enzymes, according to the following steps:
a. harvesting cells of the Cyanobacteria;
b. adding the construct to the harvested Cyanobacteria cells;
c. incubating the construct and the Cyanobacteria cells such that the construct is transformed into the Cyanobacteria cells;
d. plating the incubated constructs and Cyanobacteria cells on plates containing ampicillin and incubating under appropriate growth conditions;
e. selecting the transformed ampicillin resistant Cyanobacteria cells.

In a further aspect of the present invention, there is provided a process for producing ethanol using genetically modified Cyanobacteria which comprises the steps of: culturing in a culture medium Cyanobacteria, wherein the Cyanobacteria contains a construct comprising DNA fragments encoding pdc and adh enzymes obtained from the Zymomonas mobiles pLOI295 and accumulating ethanol in the culture medium. In a preferred embodiment, the process for producing ethanol includes a construct which comprises a temperature inducible gene and the process comprises the further step of increasing the temperature of the culture medium to induce expression of the pdc and adh genes.

DETAILED DESCRIPTION OF THE DRAWINGS

The invention will now be better understood with reference to the following figures and examples, and corresponding description, which are illustrative of preferred embodiments of the invention. The invention should not be limited by the drawings.

FIG. 9 is a description of the pdc gene identified as SEQ ID. No. 5.

Figure 1:
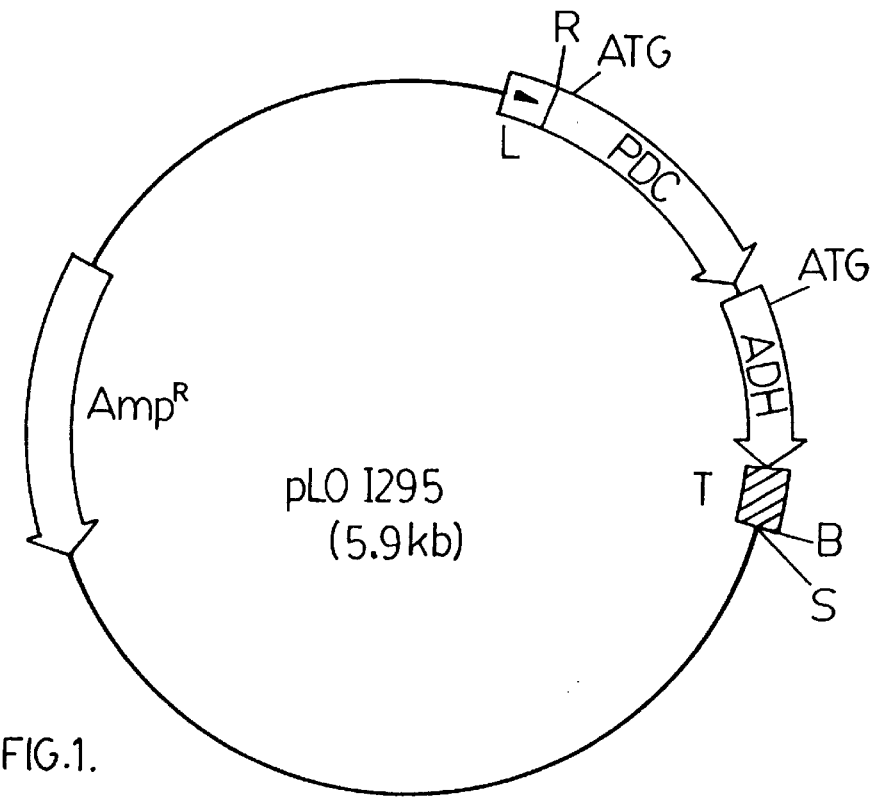
FIG. 1 is an illustration of the map of the plasmid pLOI295 containing the DNA fragments encoding for pdc and adh.

FIG. 10 is a description of the adh gene identified as SEQ. ID. No. 6.

FIG. 11 is a description of the CI-PL promoter identified as SEQ. ID. No. 7.

All like letter designations refer to the same sites on the different maps of the plasmid constructs in the figures as follows: $AMP^R$ (ampicillin resistant); PDC (pyruvate decarboxylase); ADH (alcohol dehydrogenase); ATG (start codon); L (lacZ promoter); R (rbcLS promoter); R' (EcoRI); B (BamHI); S (SalI); X (XbaI); X/P (XbaI/PvuII fusion); Xh/B (XhoI/BamHI fusion); T (transcription terminator) and CI-PL (temperature inducible gene and bacterial phage left-ward promoter).

DETAILED DESCRIPTION

Cyanobacteria are photosynthetic bacteria which require light, inorganic elements, water and a carbon source, generally $CO_2$, to metabolise and grow.

Cyanobacteria are photosynthetic procaryotes which carry out oxygenic photosynthesis. The main product of the metabolic pathway of Cyanobacteria during aerobic conditions is oxygen and carbohydrate reserves.

The initial product of photosynthetic fixation of $CO_2$ is 3-phosphoglycerate. 3-phosphoglycerate is used in the Calvin Cycle to regenerate ribulose-1,5-biphosphate, which is the acceptor of $CO_2$. There are two major branching points where the intermediates of the Calvin Cycle are connected to other metabolic pathways. At one point, fructose-6-phosphate is converted into glucose-6-phosphate and glucose-phosphate, which are the substrates for the pentose phosphate pathway, the synthesis of cellulose (a major component of the cell wall) and the synthesis of glycogen (the major form of carbohydrate reserve). At the other branching point, 3-phosphoglycerate is converted into 2-phosphoglycerate, phosphoenolpyruvate and pyruvate in a sequence of reactions catalysed by phosphoglycerate mutase, enolase and pyruvate kinase, respectively. Pyruvate is directed to the partial TCA cycle for the synthesis of amino acids, nucleotides, etc. in aerobic conditions. Pyruvate is also the substrate for ethanol synthesis.

To convert the carbohydrate reserves into ethanol, the carbohydrate reserves must be diverted to the glycolytic pathway. The presumed pathway for carbohydrate reserve metabolism in Cyanobacteria is through both the glycolytic pathway and the phosphogluconate pathway. For the purposes of ethanol formation, the glycolytic pathway is of primary importance. Although not well characterized in Cyanobacteria, glycogen is presumed to be metabolized into glucose 1-phosphate by a combination of glycogen phosphorylase and a 1,6-glycosidase. Phosphoglucomutase, phosphoglucoisomerase and phosphofructokinase convert glucose 1-phosphate into a molecule of fructose1,6-bisphosphate. This compound is cleaved by the action of aldolase and triose phosphate isomerase into two molecules of glyceraldehyde 3-phosphate. This compound is converted into pyruvate through sequential series of reactions catalysed by glyceraldehyde 3-phosphate dehydrogenase, phosphoglycerate kinase, phosphoglycerate mutase, enolase and pyruvate kinase, respectively.

In some algae and Cyanobacteria strains, a small amount of ethanol is synthesized as a fermentation product under dark and anaerobic conditions (Van der Oost et al., 1989; Heyer and Krumbein, 1991). However, the dark-anaerobic fermentation process is generally operating at a very low level, only sufficient for the survival of the organisms under such stress conditions. The synthesis of ethanol under dark and anaerobic conditions is dependent on the degradation of glycogen reserve, as described above. Moreover, it has been found that ethanol synthesis under anaerobic conditions is totally inhibited by light. Thus, in photosynthetic microorganisms ethanol synthesis is not coupled with photosynthesis and can actually be inhibited by photosynthesis.

Therefore, it has been observed that Cyanobacteria do not utilize $CO_2$ to produce ethanol. Furthermore, there are no known photosynthetic microorganisms, including genetically engineered photosynthetic microorganisms, which produce ethanol in relatively substantial amounts. A further complication is that some photosynthetic organisms have been shown to be inhibited by ethanol such that the addition of ethanol to the culture medium inhibits the expression of genes involved in photosynthesis.

In the present invention, it has been found that Cyanobacteria can be successfully genetically engineered to utilize a direct flux of carbon from $CO_2$ to 3-phosphoglycerate, and to pyruvate, to produce a quantifiable amount of ethanol as opposed to utilizing a glycogen reserve as is done under anaerobic and dark conditions.

It has been found that Cyanobacteria can be genetically modified by introducing genes encoding for the enzymes pdc and adh to produce ethanol. In particular, a pathway for ethanol synthesis has been created in Synechococcus PCC 7942, and this pathway is directly coupled with photosynthesis.

By incorporating the genetic material encoding the pdc and adh enzymes into the Synechococcus genetic material, a Synechococcus capable of producing ethanol is created. It was surprisingly found that pdc and adh enzymes from an obligate anaerobe, Z. mobilis, could be successfully inserted, expressed and be fully functional in Synechoccocus. Although pdc and adh enzymes from Z. mobilis had been transformed into E. coli. As described in Ingram, et al. (1987), "Genetic Engineering of Ethanol Production in Escherichia coli" (Appl. Environ Microbiol. 53: 2420–2425), E. coli is a facultative anaerobic, it has an inducible adh gene and it is grown in a carbohydrate medium and said carbohydrates are used to produce ethanol. On the other hand, Cyanobacteria are photosynthetic organisms and are recalcitrant to taking up organic substances for any purpose, including growth or ethanol production. Hence, E. coli is a very different system than Cyanobacteria. E. coli is more like Z. mobilis which depends on feed stock for growth and ethanol production. There are other sources of pdc and adh enzymes, including Saccharomyces cerevisciae.

It has also been found that ethanol synthesis may compete with cell growth for the use of carbon. Therefore, it would be beneficial to have an inducible system for ethanol synthesis so that cell growth and ethanol synthesis could be carried out in two phases. During the first phase, Cyanobacteria cells are cultured under non-induced conditions, so that the cell culture can reach a high density and accumulate a large amount of carbohydrates. Ethanol synthesis is then induced in the second phase.

In particular it was discovered that a temperature inducible system could be successfully developed to induce the production of ethanol in Cyanobacteria. A pdc-adh operon with the bacterial phage left-ward promoter ($P_L$) and a temperature sensitive repressor gene CI857 were employed to produce a temperature inducible system for producing ethanol in Cyanobacteria.

It is believed that at a non-permissible temperature (low temperature, 30 degrees Celsius), the repressor binds to the operator sequence, and thus prevents RNA polymerase from initiating transcription at the $P_L$ promoter. Therefore, the expression of pdc-adh genes is repressed. When the cell culture is transferred to a permissible temperature (37–42 degrees Celsius), the repressor can not bind to the operator. Therefore, RNA polymerase can initiate the transcription of the pdc-adh gene.

The Examples below exemplify the four different constructs: pCB4-Rpa, pCB4-LRpa, pCB4-LR(TF)pa and pCB4-CPpa: the synthesis of these constructs; the incorporation of these constructs into Synechococcus PCC 7942 and the production of ethanol from said genetically modified Synechococcus. Other transformable strains of Synechoccocus which are capable of producing ethanol when a construct containing DNA encoding the adh and pdc enzyme is transformed into the Synechococcus may also be used.

In the examples below, Synechococcus PCC 7942, which is available from the Pasteur Culture Collection, Rue de Dr. Roux, Paris, France, was used. The genes encoding the pdc and adh enzymes of Zymomonas mobilis were excised from the pLOI295 plasmid, which is available from Dr. L. O. Ingram, Dept. of Microbiology and Cell Science, University of Florida, Gainsville, Fla., U.S.A. 32611. (See also: Ingram et al., (1987) "Genetic Engineering of Ethanol Production in Escherichia coli" Appl. Environ Microbial 53: 2420–2425).

A map of the pLOI295 plasmid is illustrated in FIG. 1. In particular, the DNA segment excised from the pLOI295 plasmid includes the pdc sequence starting at −46 bp (relative to the transcription start site) to a position +27 bp after the translation stop codon and is listed in EMBL as Accession No. M15393 and the DNA adh sequence starting from −31 bp up from the ATG initiation codon to +164 bp after the translation stop codon, which is listed in EMBL as Accession No. M15394.

EXAMPLE 1
pCB4-Rpa

The pCB4-Rpa construct is driven by a promoter obtained from the rbcLS operon of the cyanobacterium Synechococcus PCC 7942. The promoter sequence from the rbcLS operon was amplified from Synechococcus PCC 7942 by the polymerase chain reaction (PCR) using the forward primer identified as SEQ ID No. 1 (containing a BamHI site) and the reverse primer identified as SEQ ID No. 2 (containing an EcoRI site). These primers were designed according to the rbcL gene sequence obtained from the cyanobacterium *Anacystis nidulan* 6301, a strain genetically similar to Synechococcus PCC 7942. (Shinozaki K. et al. (1983) "Molecular cloning and sequence analysis of the Cyanobacteria gene for the large subunit of ribulose-1,5-bisphosphate carboxylase-oxygenase." Proc Natl Acad Sci USA 80:4050–4054). The PCR reaction mixture (100 µl) contained 0.5 µM of each primer, 0.4 mM dNTP, 10 ng genomic DNA from Synechococcus sp. PCC 7942 and 2 units of $Vent_R$ DNA plolymerase (New England Biolabs) in 1×reaction buffer: 10 mM KCl, 10 mM $(NH_4)_2SO_4$, 20 mM Tris-HCl (pH 8.8 at 25° C.), 2 mM $MgCl_2$ and 0.1% Triton X-100. PCR reactions were carried out in PTC-100TM Programmable Thermal Controller (MJ Research, Inc.) by using the temperature cycles as follows: 93° C./3 min; 30 cycles of 93° C./1 min, 62° C./1.5 min, 72° C./5. The PCR product of expected size was cloned into the BamHI-EcoRI sites of the plasmid pBlueScript SK (Stratagene Inc.) to generate a plasmid designated pRBCp.

Figure 2:
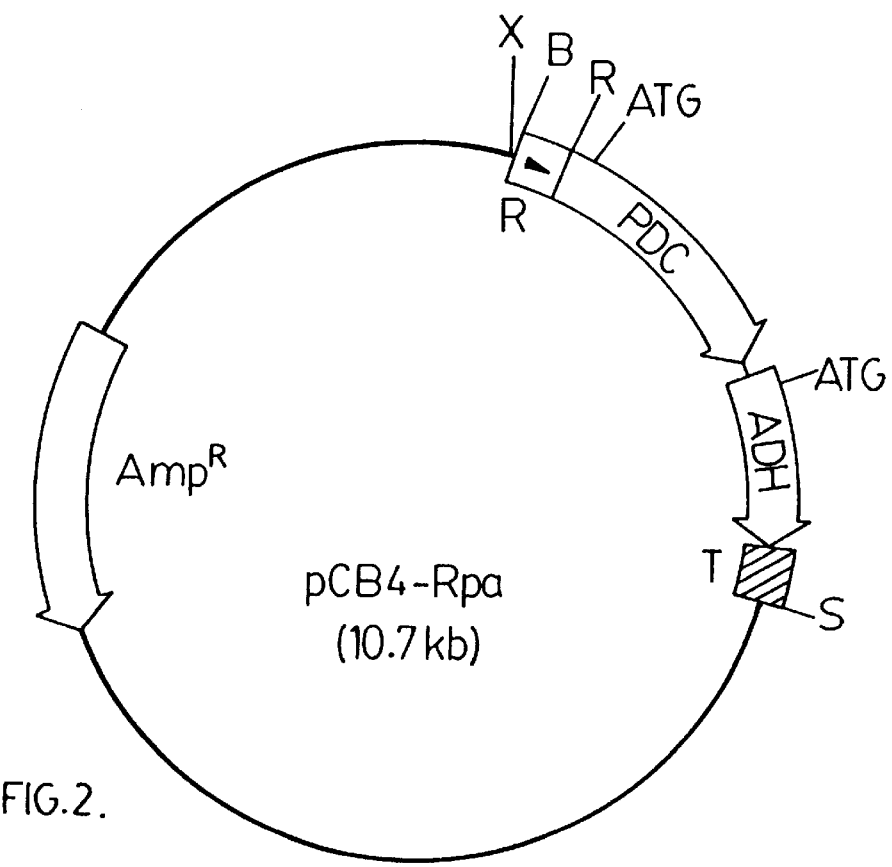
FIG. 2 is an illustration of the map of the plasmid construct pCB4-Rpa.

A 3.2 kbp EcoRI-SalI DNA fragment containing the pdc-adh sequence from *Zymomonas mobilis* was isolated from the pLOI295 plasmid and ligated into the corresponding sites of pRBCp to generate the plasmid pRpa. The pLOI295 plasmid map is illustrated in the map in FIG. 1. A 3.6 kbp BamHI DNA fragment containing the rbcLS promoter region and the pdc-adh sequences were then excised from pRpa and ligated into the BamHI site of the shuttle vector pCB4 (Gendel et al., (1983) "Shuttle Cloning Vectors for the Cyanobacterium *Anacystis Vidulans*", J. Bacteriol, 156: 148–154) resulting in the vector construct pCB4-Rpa. The shuttle vector pCB4 contains genes encoding ampicillan resistance. The vector construct pCB4-Rpa is illustrated in FIG. 2.

EXAMPLE 2
pCB4-LRpa

Figure 3:
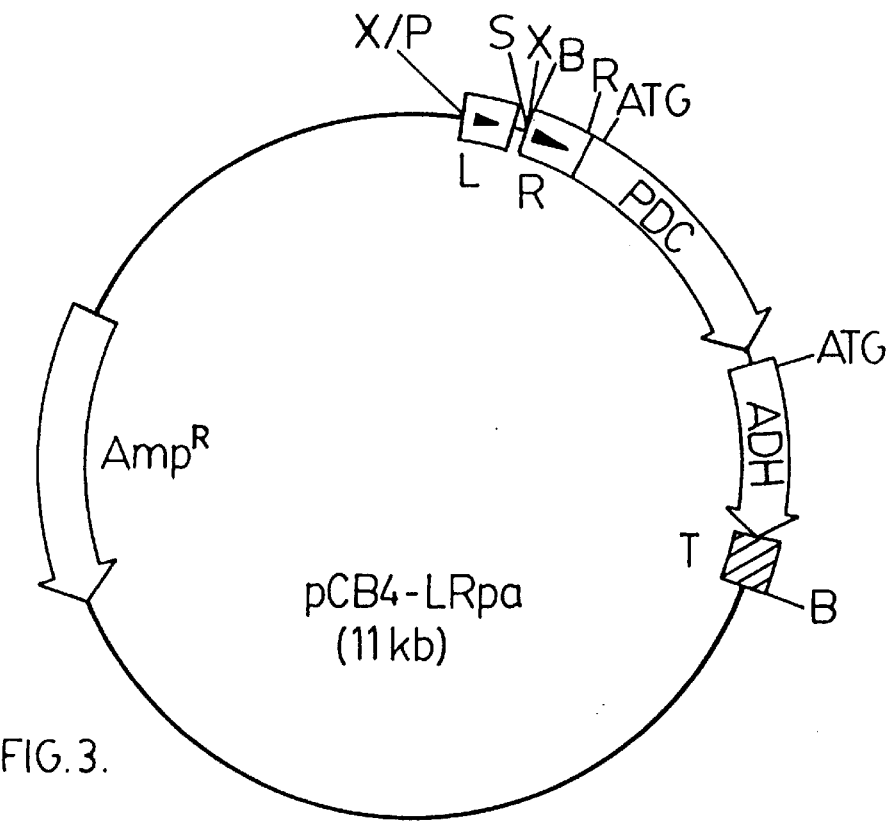
FIG. 3 is an illustration of the map of the plasmid construct pCB4-LRpa.

A 3.6 kbp BamHI DNA fragment from pRpa was ligated into a modified version of pCB4. The modified version of pCB4 is constructed by ligating a 220 bp PvuII-BamHI DNA fragment from the plasmid pBS (Stratagene Inc., 11011 North Torrey Pines Road, La Jolla, Calif., U.S.A. 92037), which fragment contains the lacZ promoter region from *Escherichia coli*, into the modified XbaI-BamHI sites of the pCB4 multi-cloning site. (Soltes-Rak E et al. (1993) "Effect of promoter modification on mosquitocidal cryIVB gene expression in Synechococcus sp. strain PCC 7942." Appl Environ Microbio. 59: 2404–2410). The 3.6 kbp DNA fragment is then ligated into the modified version of pCB4 resulting in the vector construct pCB4-LRpa. The vector construct pCB4-LRpa is illustrated in FIG. 3.

EXAMPLE 3
pCB4-LR(TF)pa

The pdc-adh coding region is driven by a combination of the rbcLS and lacZ promoter regions, as in pCB4-LRpa, but in this construct the *Zymomonas mobilis* pdc ribosome binding site and start codon have been removed and replaced with the corresponding DNA region of the rbcL sequence from Synechococcus PCC 7942 to generate a translation fusion product.

Figure 4:
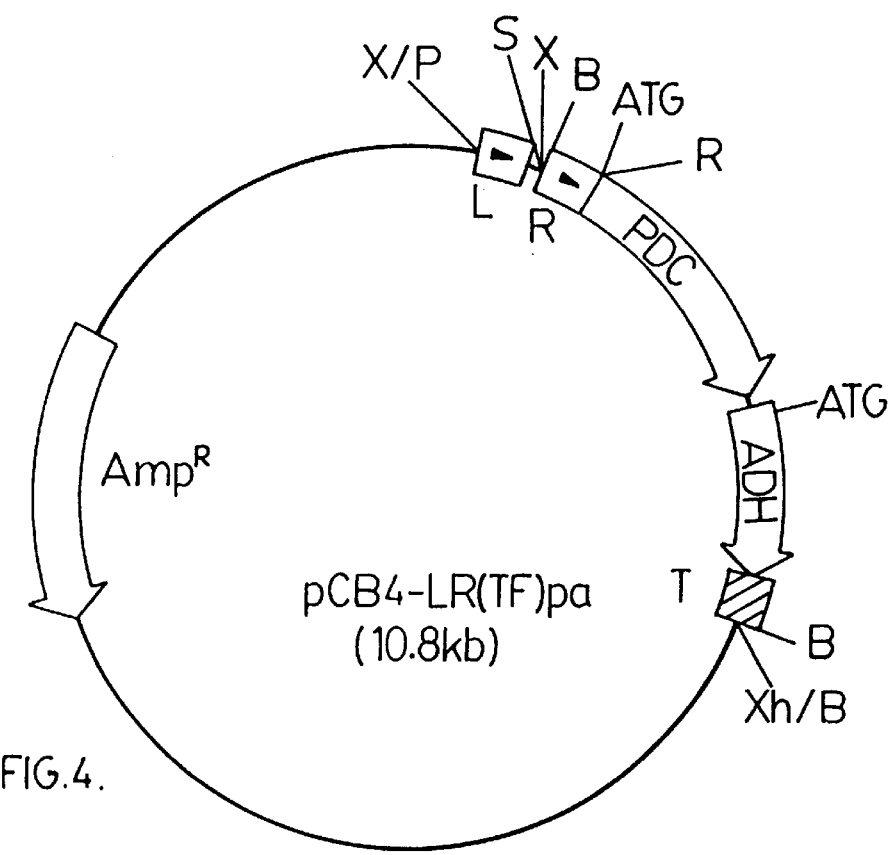
FIG. 4 is an illustration of the map of the plasmid construct pCB4-LR(TF)pa.
Figure 5:
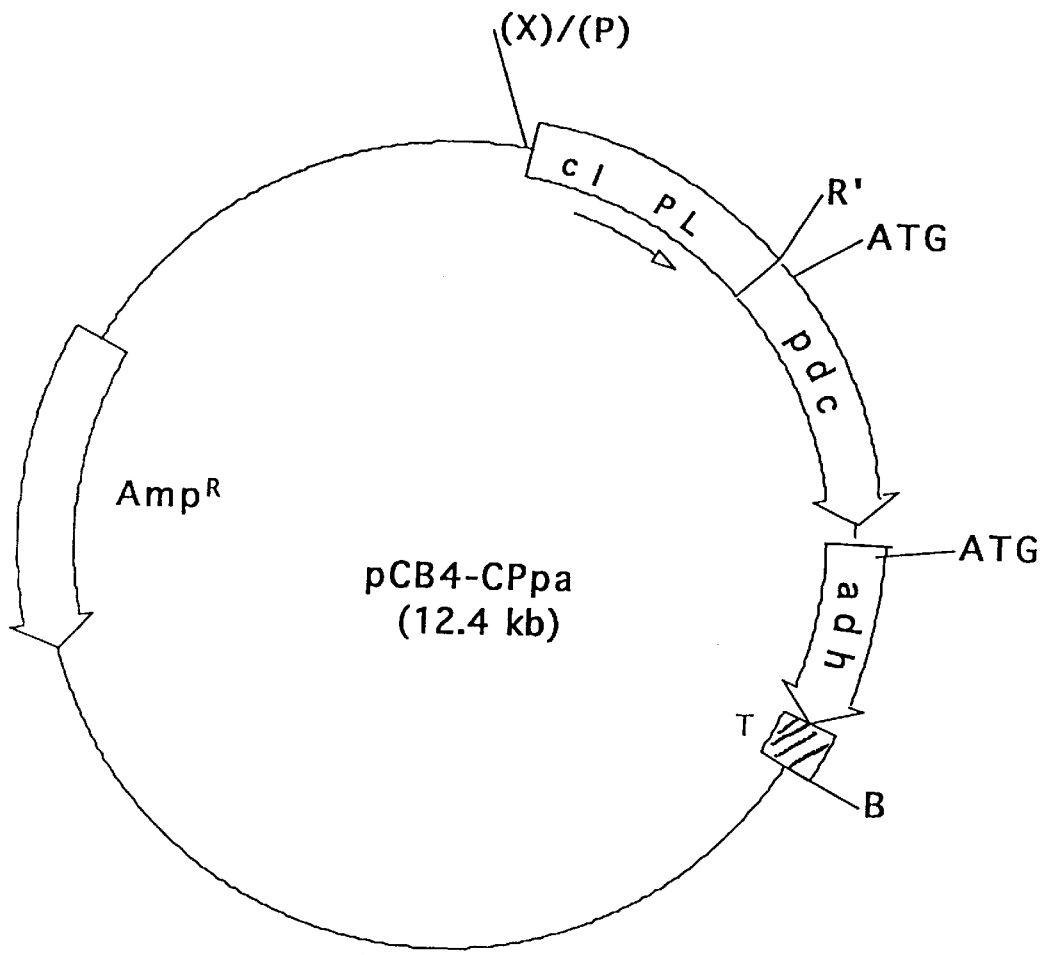
FIG. 5 is an illustration of the map of the plasmid construct pCB4-CPpa.

The pdc-adh DNA segment in pLOI295 plasmid is amplified and modified by PCR using the forward primer identified as SEQ ID No. 3 (containing an EcoRI site) and reverse primer identified as SEQ ID No. 4 (containing BamHI and XhoI sites). The PCR reaction mixture was as described above for Example 1. The temperature cycles were as follows: 93° C./5 min; 4 cycles of 93° C./1 min, 56° C./1.5 min, 72° C./3.5 min; 30 cycles of 93° C./1 min, 65° C./1.5° C., 72° C./3.5 min; 72° C./5 min. The 3.1 kbp PCR product was then ligated into pRBCp at the EcoRI-XhoI sites (double-cut) to generate plasmid pR(TF)pa (TF as in Translation Fusion). The cloning for translation fusion generated an extra codon AAT (asparagine) immediately after the initiation codon and the original second codon, AGT in pdc open reading frame was replaced by TCT to code the same amino acid (serine). This new plasmid was digested with XhoI, the cut sites blunt ended with Klenow fragment from DNA polI, and then digested with XbaI. This DNA fragment containing rbc-(TF)pdc-adh was then ligated into pCB4-lac which had been prepared by digestion with BamHI, blunt ended with Klenow, and redigested with XbaI. The resulting plasmid is designated pCB4-LR(TF)pa and is illustrated in FIG. 4.

EXAMPLE 4
pCB4-CPpa

The vector pCB4-Rpa was digested with XbaI, end-filled with Klenow fragment of DNA polymerase I and re-digested with EcoRI to delete the rbcLS promoter. The vector was then ligated to a PstI-EcoRI fragment containing the CI857 repressor gene and $P_L$ promoter sequence, collectively termed the cI-PL gene sequence (EMBL Accession No. L05669; Sanger et al. *Nucleotide* sequence of the bacteriophage lambda DNA. 1982, J. Mole. Biol. 162: 729–773) and identified as SEQ. ID. No. 7. The $P_L$ promoter had been isolated from the plasmid pHUB2-CI857 (Gruber et al. (1991)) "*Escherichia coli-Anacystis nidulans* plasmid shuttle vectors containing the $P_L$ promoter from bacteriophage lambda." Curr. Microbio. 22:15–19). The vector was ligated by digestion with PstI, end-filling with Klenow and a second digestion with EcoRI. The recombinant plasmid is designated as pCB4-CPpa.

EXAMPLE 5
Genetically Modified Synechococcus PCC 7942

Each of the four constructs of Examples 1, 2, 3 and 4 were incorporated into the Synechococcus PCC 7942.

The constructs of Examples 1, 2, 3 and 4 were incorporated into the Synechococcus is PCC 7942 using a standard protocol as set out in Golden SS et al. (1987) "Genetic engineering of the Cyanobacteria chromosome" Methods Enzymol 153:215–231 and in S. S. Golden and L. A. Sherman, J. Bacteriology 158:36 (1984), incorporated herein by reference. Briefly, cells of Synechococcus PCC 7942 are harvested by centrifugation and re-suspended in BG-11 medium at a concentration of $2–5\times10^8$ cells per ml. To one ml of this cell solution is added the appropriate plasmid construct DNA to a final concentration of $2 \mu g.ml^{-1}$. Cells are incubated in the dark for 8 hours followed by a 16 h light incubation prior to plating on BG-11 plates containing 1 µg.ml$^{-1}$ ampicillin. Plates are incubated under the standard growth conditions (30° C. light intensity of 100 µmol photons. m$^{-2}$.s$^{-1}$). Ampicillin resistant colonies were visible in 7–10 days.

Figure 6:
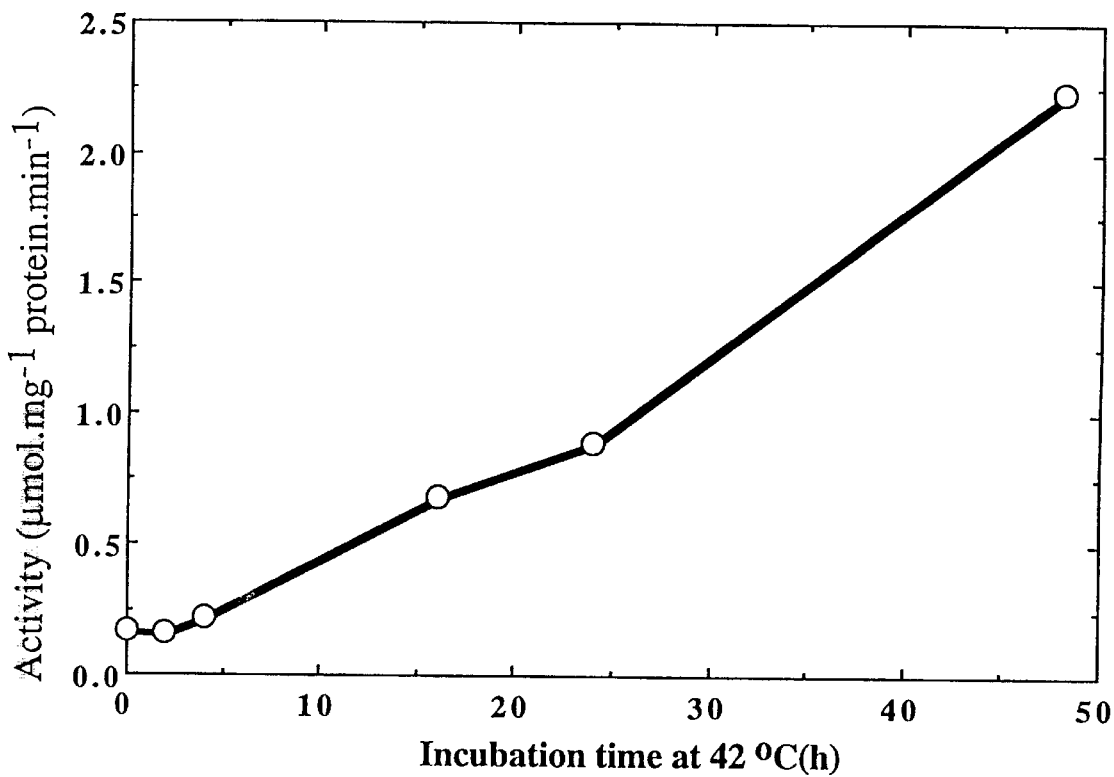
FIG. 6 is an illustration of a graph of the incubation time of Synechococcus PCC 7942 cells transformed with the vector pCB4-CPpa. at 42 degrees Celsius versus the activity of pyruvate decarboxylase.
Figure 7:
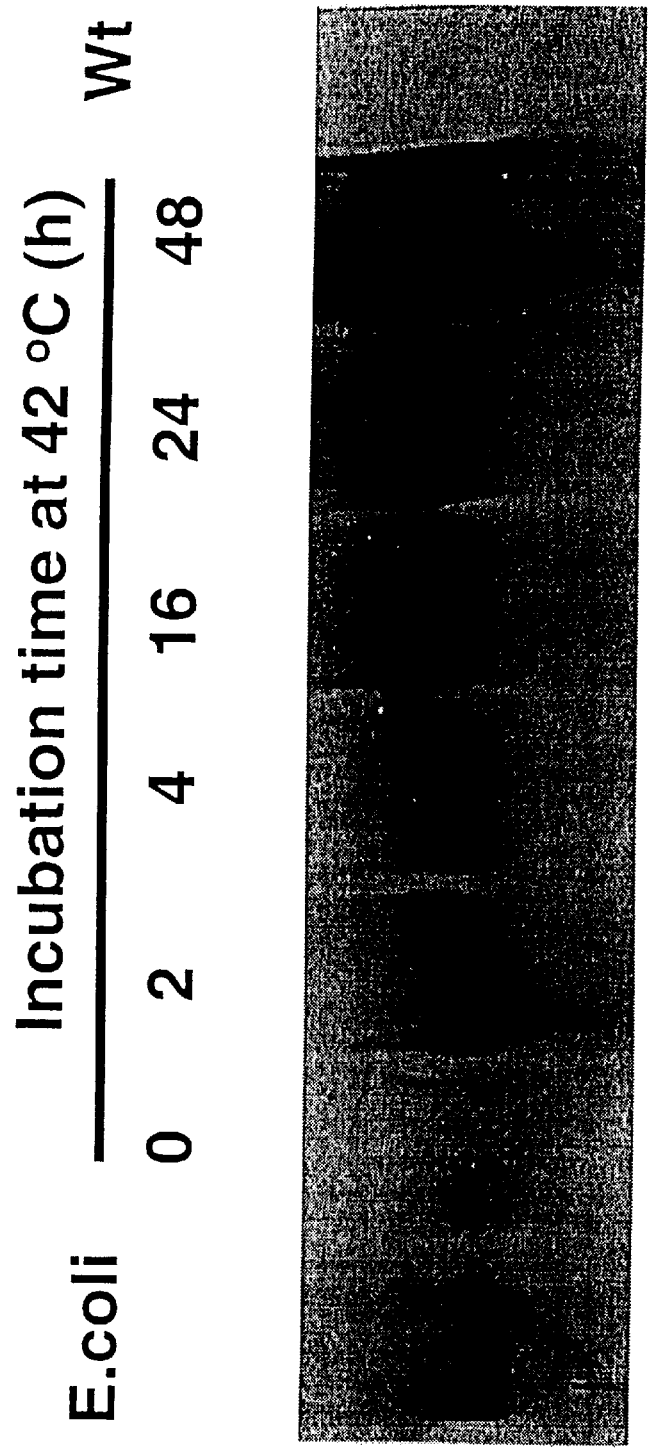
FIG. 7 is an illustration of the induction of adh expression at 42 degrees Celsius for Synechococcus PCC 7942 as compared to E. coli and wild type Synechococcus.
Figure 8:
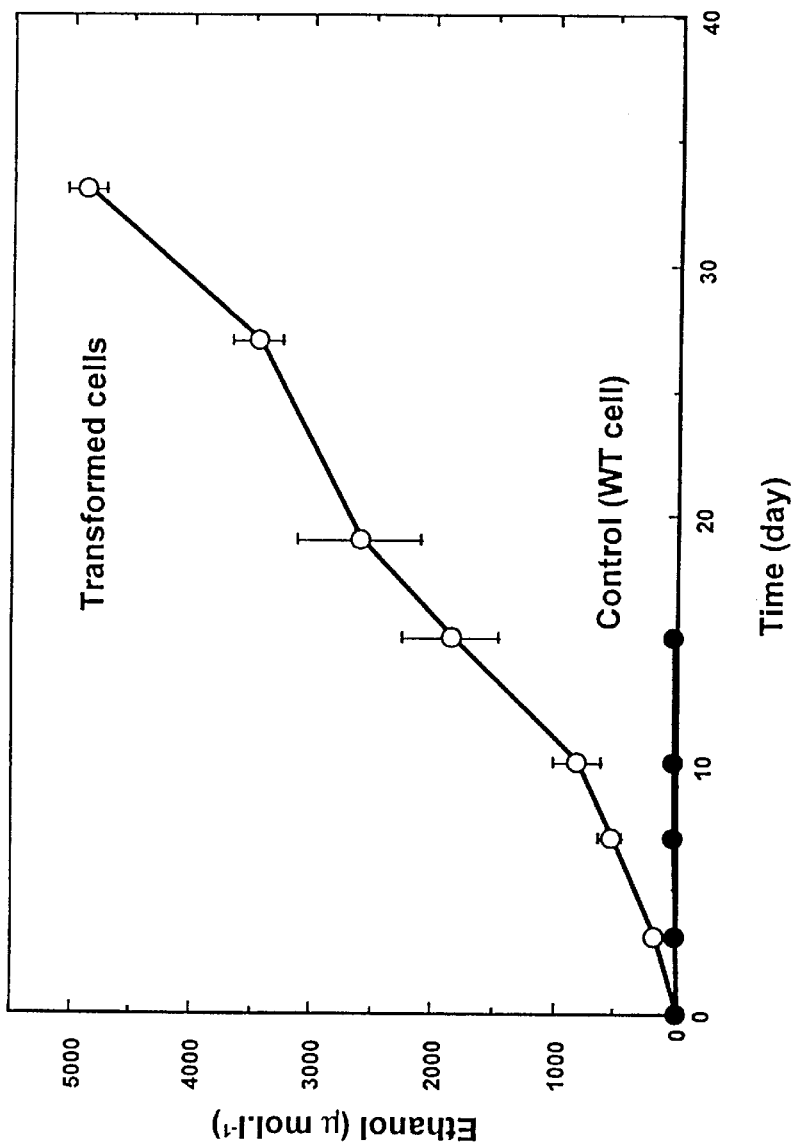
FIG. 8 is an illustration of the induction time of Synechococcus PCC 7942 versus ethanol production in Synechoccus PCC 7942 in cells transformed with pCB4-Rpa.

The genetically modified Synechococcus PCC 7942 were grown, bubbling with air at 30 and a light intensity of 100 µE.M$^{-2}$.s$^{-1}$ in liquid BG-11 medium containing 5 µg.ml$^{-1}$ ampicillin (Soltes-Rak E et al. (1993) "Effect of promoter modification on mosquitocidal cryIVB gene expression in Synechococcus sp. strain PCC 7942." Appl Environ Microbio. 59:2404–2410) The activity of pdc, adh and the production of ethanol were measured as set out in Table 1 below for Examples 1, 2 and 3. The ethanol production for Example 3 is also illustrated in FIG. 8. Table 2 illustrates the ethanol production for Example 4. FIGS. 6 and 7 illustrate the pdc activity and adh expression, respectively, for Example 4. The activity of pdc was measured by determining the rate of pyruvic acid dependent reduction of NAD$^+$ with yeast with adh as the coupling enzyme as previously described in Conway et al., J. Bacteriology 169:2591–2597 (1987). Adh was measured for Examples 1, 2 and 3 by determining the rate of ethanol dependent NADH oxidation as described in Neale et al., Eur. J. Biochem. 154: 119–124 (1986). Ethanol was assayed using a standard Ethanol Assay kit obtained from Boehringer Mannheim Canada, Laval, Quebec. The results of the tests for pdc and adh activity and ethanol production for the constructs of Examples 1–3 are illustrated in Table 1.

TABLE 1

| Constructs | PDC Activity nmol · min.$^{-1}$ · mg$^{-1}$ SP$^1$ | ADH Activity nmol · min.$^{-1}$ · mg$^{-1}$ SP | Ethanol Conc. in medium (µM)$^3$ | Ethanol Conc. in µmoL · mg$^{-1}$ Chlorophyll |
|---|---|---|---|---|
| pCB4$^4$ | ND$^2$ | ND | ND | ND |
| pCB4-Rpa | 130 | 168 | 1370 | 274 |
| pCB4-LRpa | 136 | 168 | 1540 | 308 |
| pCB4-LR(TF)pa | 234 | 168 | 1710 | 342 |

$^1$SP, soluble protein.
$^2$ND, not detectable.
$^3$Represents ethanol concentration in medium following 21 days growth in batch culture at a final cell density of OD$_{730}$1.5. This OD represents approximately 5 × 10$^8$ cells.ml$^{-1}$. Values in table are an underestimation of ethanol concentration as some ethanol is lost from the unsealed culture vessels during aeration. Concentrations approximating 5 mM can be achieved following 28 days of growth.
$^4$Synechococcus PCC 7942 cells transformed with the shuttle vector pCB4 alone.

Synechococcus PCC 7942 cells were transformed with the vector pCB4-CPpa. The transformed cells were first grown at 30 degrees Celsius as set out above and then transferred to 42 degrees Celsius for 48 hours. Cells were harvested at intervals to assay pdc activity. As shown in FIG. 6, pdc activity was induced at 42 degrees, reaching a 20-fold increase at 48 hours after the temperature shift. Surprisingly, the pdc activity induced at 42 degrees Celsius with the pCB4-CPpa vector after 48 hours was approximately 2000 nmol.min.$^{-1}$.mg$^{-1}$ SP, which is about 20-fold higher than in the strain harboring the shuttle vector pCB4-Rpa which had a pdc activity of approximately 130 nmol.min.$^{-1}$.mg$^{-1}$ SP as can be seen in FIG. 6 and Table 1, respectively.

The impact of temperature shift on ethanol synthesis was studied in liquid batch culture. The rate of ethanol synthesis at 42 degrees Celsius was 1.7 µmol ethanol per mg of chlorophyll per hour. As such, it was 5-times higher at 42 degrees than at 30 degrees Celsius, as can be seen in Table 2.

TABLE 2

Effect of temperature shift on Ethanol Synthesis
Synechococcus PCC 7942 cells transformed with the shuttle vector pCB4-CPpa were first grown at 30 deg. Celsius in the light, harvested at log phase and resuspended into a fresh medium at a cell density of 4.3 µg chlorophyll per ml. The resuspended cells were grown for 48 h in the light at 30 deg. Celsius and 42 deg. Celsius, respectively. The value in the brackets indicates the S.D. for 4 different samples.

| Temperature | Ethanol Conc. (µmol · mg$^{-1}$ chlorophyll) | Rate of Ethanol Synthesis (µmol · mg$^{-1}$ chlorophyll per hr) |
|---|---|---|
| 30 | 16(0.9) | 0.33 |
| 42 | 82(8.9) | 1.70 |

The above examples are intended to exemplify the invention. It is understood by the skilled workman in the art that various modifications and alterations may be made without departing from the scope of the invention and as set out in the claims attached hereto.

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
      (A) LENGTH: 29 base pairs
      (B) TYPE: nucleic acid
      (C) STRANDEDNESS: single (D) TOPOLOGY: linear (ii) MOLECULE TYPE: cDNA (xi) SEQUENCE DESCRIPTION: SEQ ID NO: 1:

GCTGAATTCA TGTCGTCTCT CCCTAGAGA                                              29

(2) INFORMATION FOR SEQ ID NO: 2:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 2:

GCTGAATTCA TGTCGTCTCT CCCTAGAGA                                              29

(2) INFORMATION FOR SEQ ID NO: 3:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 3:

GGACTCGAGG ATCCCCAAAT GGCAA                                                  25

(2) INFORMATION FOR SEQ ID NO: 4:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 4:

GCATGAATTC TTATACTGTC GGTACCTAT                                              29

(2) INFORMATION FOR SEQ ID NO: 5:

(i) SEQUENCE CHARACTERISTICS:
            (A) LENGTH: 1905 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 5:

TATCGCTCAT GATCGCGACA TGTTCTGATA TTTTCCTCTA AAAAAGATAA AAAGTCTTTT            60

CGCTTCGGCA GAAGAGGTTC ATCATGAACA AAAATTCGGC ATTTTAAAA ATGCCTATAG            120

CTAAATCCGG AACGACACTT TAGAGGTTTC TGGGTCATCC TGATTCAGAC ATAGTGTTTT           180

GAATATATGG AGTAAGCAAT GAGTTATACT GTCGGTACCT ATTTAGCGGC GCTTGTCCAG           240

ATTGGTCTCA AGCATCACTT CGCAGTCGCG GGCGACTACA ACCTCGTCCT TCTTGACAAC           300

CTGCTTTTGA ACAAAAACAT GGAGCAGGTT TATTGCTGTA ACGAACTGAA CTGCGGTTTC           360

AGTGCAGAAG GTTATGCTCG TGCCAAAGCG GACGCAGCAG CCGTCGTTAC CTACAGCGTC           420

```
GGTGCGCTTT CCGCATTTGA TGCTATCGGT GGCGCCTATG CAGAAAACCT TCCGGTTATC      480

CTGATCTCCG GTGCTCCGAA CAACAATGAT CACGCTGCTG GTCACGTGTT GCATCACGCT      540

CTTGGCAAAA CCGACTATCA CTATCAGTTG GAAATGGCCA GAACATCAC GGCCGCAGCT       600

GAAGCGATTT ACACCCCAGA GAAGCTCCG GCTAAAATCG ATCACGTGAT TAAAACTGCT       660

CTTCGTGAGA AGAAGCCGGT TTATCTCGAA ATCGCTTGCA ACATTGCTTC CATGCCCTGC      720

GCCGCTCCTG GACCGGCAAG CGCATTGTTC AATGACGAAG CCAGCGACGA AGCTTCTTTG      780

AATGCAGCGG TTGAAGAAAC CCTGAAATTC ATCGCCAACC GCGACAAAGT TGCCGTCCTC      840

GTCGGCAGCA AGCTGCGCGC AGCTGGTGCT GAAGAAGCTG CTGTCAAATT TGCTGATGCT      900

CTCGGTGGCG CAGTTGCTAC CATGGCTGCT GCAAAAAGCT TCTTCCAGAA GAAAACCGCA      960

TTACATCGGT ACCTCATGGG TGAAGTCAGC TATCCGGGCG TTGAAAAGAC GATGAAAGAA     1020

GCCGATGCGG TTATCGCTCT GGCTCCTGTC TTCAACGACT ACTCCACCAC TGGTTGGACG     1080

GATATTCCTG ATCCTAAGAA ACTGGTTCTC GCTGAACCGC GTTCTGTCGT CGTTAACGGC     1140

GTTCGCTTCC CCAGCGTTCA TCTGAAAGAC TATCTGACCC GTTGGCTCA GAAAGTTTCC      1200

AAGAAAACCG GTGCTTTGGA CTTCTTCAAA TCCCTCAATG CAGGTGAACT GAAGAAAGCC     1260

GCTCCGGCTG ATCCGAGTGC TCCGTTGGTC AACGCAGAAA TCGCCCGTCA GGTCGAAGCT     1320

CTTCTGACCC CGAACACGAC GGTTATTGCT GAAACCGGTG ACTCTTGGTT CAATGCTCAG     1380

CGCATGAAGC TCCCGAACGG TGCTCGCGTT GAATATGAAA TGCAGTGGGG TCACATCGGT     1440

TGGTCCGTTC CTGCCGCCTT CGGTTATGCC GTCGGTGCTC CGGAACGTCG CAACATCCTC     1500

ATGGTTGGTG ATGGTTCCTT CCAGCTGACG GCTCAGGAAG TCGCTCAGAT GGTTCGCCTG     1560

AAACTGCCGG TTATCATCTT CTTGATCAAT AACTATGGTT ACACCATCGA AGTTATGATC     1620

CATGATGGTC CGTACAACAA CATCAAGAAC TGGGATTATG CCGGTCTGAT GGAAGTGTTC     1680

AACGGTAACG GTGGTTATGA CAGCGGCGCT GGTAAAGGCC TGAAGGCTAA AACCGGTGGC     1740

GAACTGGCAG AAGCTATCAA GGTTGCTCTG GCAAACACCG ACGGCCCAAC CCTGATCGAA     1800

TGCTTCATCG GTCGTGAAGA CTGCACTGAA GAATTGGTCA AATGGGGTAA GCGCGTTGCT     1860

GCCCGCCAAC AGCCGTAAGC CTGTTAACAA GCTCCTCTAG TTTTT                     1905
```

(2) INFORMATION FOR SEQ ID NO: 6:

(i) SEQUENCE CHARACTERISTICS:
        (A) LENGTH: 1747 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

```
AAAGGCAAAA TCGGTAACCA CATCTCAATT ATTAAACAAT ACTTCATAAT AAAAAGACAA       60

CTTTTTCATA ATTTGCATAA GTCTTGATGT AAAAAATACA TATTTAGAAA GAACAAGCAG      120

CCTTGCTCAT CACCGCTGTC GCGAGTAGAA AAATCTCGGC TTTCAGAAAA AGAGGCCGCT      180

TCGTTAAACA GACTATAAAT GTGCTGGAAT AAAGCGAACC CCTTGATCTG ATAAAACTGA      240

TAGACATATT GCTTTTGCGC TGCCCGATTG CTGAAAATGC GTAAAGGTG ATTTTACTCG       300

TTTTCAGGAA AAACTTTGAG AAAACGTCTC GAAAACGGGA TTAAAACGCA AAACAATAG       360

AAAGCGATTT CGCGAAAATG GTTGTTTTCG GGTTGTTGCT TTAAACTAGT ATGTAGGGTG      420

AGGTTATAGC TATGGCTTCT TCAACTTTTT ATATTCCTTT CGTCAACGAA ATGGGCGAAG      480
```

-continued

```
GTTCGCTTGA AAAAGCAATC AAGGATCTTA ACGGCAGCGG CTTTAAAAAT GCGCTGATCG    540

TTTCTGATGC TTTCATGAAC AAATCCGGTG TTGTGAAGCA GGTTGCTGAC CTGTTGAAAG    600

CACAGGGTAT TAATTCTGCT GTTTATGATG GCGTTATGCC GAACCCGACT GTTACCGCAG    660

TTCTGGAAGG CCTTAAGATC CTGAAGGATA ACAATTCAGA CTTCGTCATC TCCCTCGGTG    720

GTGGTTCTCC CCATGACTGC GCCAAAGCCA TCGCTCTGGT CGCAACCAAT GGTGGTGAAG    780

TCAAAGACTA CGAAGGTATC GACAAATCTA AGAAACCTGC CCTGCCTTTG ATGTCAATCA    840

ACACGACGGC TGGTACGGCT TCTGAAATGA CGCGTTTCTG CATCATCACT GATGAAGTCC    900

GTCACGTTAA GATGGCCATT GTTGACCGTC ACGTTACCCC GATGGTTTCC GTCAACGATC    960

CTCTGTTGAT GGTTGGTATG CCAAAAGGCC TGACCGCCGC CACCGGTATG GATGCTCTGA   1020

CCCACGCATT TGAAGCTTAT TCTTCAACGG CAGCTACTCC GATCACCGAT GCTTGCGCCT   1080

TGAAGGCTGC GTCCATGATC GCTAAGAATC TGAAGACCGC TTGCGACAAC GGTAAGGATA   1140

TGCCAGCTCG TGAAGCTATG GCTTATGCCC AATTCCTCGC TGGTATGGCC TTCAACAACG   1200

CTTCGCTTGG TTATGTCCAT GCTATGGCTC ACCAGTTGGG CGGCTACTAC AACCTGCCGC   1260

ATGGTGTCTG CAACGCTGTT CTGCTTCCGC ATGTTCTGGC TTATAACGCC TCTGTCGTTG   1320

CTGGTCGTCT GAAAGACGTT GGTGTTGCTA TGGGTCTCGA TATCGCCAAT CTCGGTGATA   1380

AGAAGGCGC AGAAGCCACC ATTCAGGCTG TTCGCGATCT GGCTGCTTCC ATTGGTATTC   1440

CAGCAAATCT GACCGAGCTG GGTGCTAAGA AGAAGATGT GCCGCTTCTT GCTGACCACG   1500

CTCTGAAAGA TGCTTGTGCT CTGACCAACC CGCGTCAGGG TGATCAGAAA GAAGTTGAAG   1560

AACTCTTCCT GAGCGCTTTC TAATTTCAAA ACAGGAAAAC GGTTTTCCGT CCTGTCTTGA   1620

TTTTCAAGCA AACAATGCCT CCGATTTCTA ATCGGAGGCA TTTGTTTTTG TTTATTGCAA   1680

AAACAAAAAA TATTGTTACA AATTTTTACA GGCTATTAAG CCTACCGTCA TAAATAATTT   1740

GCCATTT                                                              1747
```

(2) INFORMATION FOR SEQ ID NO: 7:

(i) SEQUENCE CHARACTERISTICS:
        (A) LENGTH: 7922 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

```
GGCGGAGTAA AAAGAGGAGC CCGGCGTCAT CTTTTGTTAC CCGCCAAACA AAACCCAAAA     60

ACAACCCATA CCCAACCCAA TAAAACACCA AAACAAGACA AATAATCATT GATTGATGGT    120

TGAAATGGGG TAAACTTGAC AAACAAACCC ACTTAAAACC CAAAACATAC CCAAACACAC    180

ACCAAAAAAA CACCATAAGG AGTTTTATAA ATGTTGGTAT TCATTGATGA CGGTTCAACA    240

AACATCAAAC TACAGTGGCA GGAAAGCGAC GGAACAATTA ACAGCACAT TAGCCCGAAC    300

AGCTTCAAAC GCGAGTGGGC AGTCCCTTTT GGTGATAAAA AGGTCTTTAA CTACACACTG    360

AACGGCGAAC AGTATTCATT TGATCCAACC AGCCCGGATG CTGTAGTCAC AACCAATATC    420

GCATGGCAAT ACAGCGACGT TAATGTCGTT GCAGTGCATC ACGCCTTACT GACCAGTGGT    480

CTGCCGGTAA GCGAAGTGGA TATTGTTTGC ACACTTCCTC TGACAGAGTA TTACGACAGA    540

AATAACCAAC CCAATACGGA AAATATTGAG CGTAAGAAAG CAAACTTCCG GAAAAAAATT    600

ACATTAAATG GCGGGGATAC ATTCACAATA AAAGATGTAA AAGTCATGCC TGAATCTATA    660
```

```
CCGGCAGGTT ATGAAGTTCT ACAAGAACTG GATGAGTTAG ATTCTTTATT AATTATAGAT    720
CTCGGGGGCA CCACATTAGA TATTTCTCAG GTAATGGGGA AATTATCGGG GATCAGTAAA    780
ATATACGGAG ACTCATCTCT TGGTGTCTCT CTGGTTACAT CTGCAGTAAA AGATGCCCTT    840
TCTCTTGCGA GAACAAAAGG AAGTAGCTAT CTTGCTGACG ATATAATCAT TCACAGAAAA    900
GATAATAACT ATCTGAAGCA ACGAATTAAT GATGAGAACA AAATATCAAT AGTCACCGAA    960
GCAATGAATG AAGCACTTCG TAAACTTGAG CAACGTGTAT TAAATACGCT CAATGAATTT   1020
TCTGGTTATA CTCATGTTAT GGTTATAGGC GGTGGCGCAG AATTAATATG CGATGCAGTA   1080
AAAAAACACA CACAGATTCG TGATGAACGT TTTTTCAAAA CCAATAACTC TCAATATGAT   1140
TTAGTTAACG GTATGTATCT CATAGGTAAT TAATGATGGA CAAGCGCAGA ACCATTGCCT   1200
TCAAACTAAA TCCAGATGTA AATCAAACAG ATAAAATTGT TTGTGATACA CTGGACAGTA   1260
TCCCGCAAGG GGAACGAAGC CGCCTTAACC GGGCCGCACT GACGGCAGGT CTGGCCTTAT   1320
ACAGACAAGA TCCCCGGACC CCTTTCCTTT TATGTGAGCT GCTGACGAAA GAAACCACAT   1380
TTTCAGATAT CGTGAATATA TTGAGATCGC TATTTCCAAA AGAGATGGCC GATTTTAATT   1440
CTTCAATAGT CACTCAATCC TCTTCACAAC AAGAGCAAAA AAGTGATGAA GAGACCAAAA   1500
AAAATGCGAC GAAGCTAATA AAATTAATTC AATTATTATT GAGTTCCCTT TATCCACTAT   1560
CAGGCTGGAT AAAGGGAACT CAATCAAGTT ATTTTCTTAC CAGTCATTAC ATAATCGTTA   1620
TTATGAAATA ATCGTTTGCA CTGTCTCTGT TATTCAGGCA ATTTCAATAA AGGCACTTGC   1680
TCACGCTCTG TCATTTTCTG AAACTCTTCA TGCTGCATTT CGCAGGTGGC ACTTTTCGGG   1740
GAAATGTGCG CGGAACCCCT ATTTGTTTAT TTTTCTAAAT ACATTCAAAT ATGTATCCGC   1800
TCATGAGACA ATAACCCTGA TAAATGCTTC AATAATATTG AAAAAGGAAG AGTATGAGTA   1860
TTCAACATTT CCGTGTCGCC CTTATTCCCT TTTTTGCGGC ATTTTGCCTT CCTGTTTTTG   1920
CTCACCCAGA AACGCTGGTG AAAGTAAAAG ATGCTGAAGA TCAGTTGGGT GCACGAGTGG   1980
GTTACATCGA ACTGGATCTC AACAGCGGTA AGATCCTTGA GAGTTTTCGC CCCGAAGAAC   2040
GTTTTCCAAT GATGAGCACT TTTAAAGTTC TGCTATGTGG CGCGGTATTA TCCCGTGTTG   2100
ACGCCGGGCA AGAGCAACTC GGTCGCCGCA TACACTATTC TCAGAATGAC TTGGTTGAGT   2160
ACTCACCAGT CACAGAAAAG CATCTTACGG ATGGCATGAC AGTAAGAGAA TTATGCAGTG   2220
CTGCCATAAC CATGAGTGAT AACACTGCGG CCAACTTACT TCTGACAACG ATCGGAGGAC   2280
CGAAGGAGCT AACCGCTTTT TTGCACAACA TGGGGGATCA TGTAACTCGC CTTGATCGTT   2340
GGGAACCGGA GCTGAATGAA GCCATACCAA ACGACGAGCG TGACACCACG ATGCCTGCAG   2400
CAATGGCAAC AACGTTGCGC AAACTATTAA CTGGCGAACT ACTTACTCTA GCTTCCCGGC   2460
AACAATTAAT AGACTGGATG GAGGCGGATA AAGTTGCAGG ACCACTTCTG CGCTCGGCCC   2520
TTCCGGCTGG CTGGTTTATT GCTGATAAAT CTGGAGCCGG TGAGCGTGGG TCTCGCGGTA   2580
TCATTGCAGC ACTGGGGCCA GATGGTAAGC CCTCCCGTAT CGTAGTTATC TACACGACGG   2640
GGAGTCAGGC AACTATGGAT GAACGAAATA GACAGATCGC TGAGATAGGT GCCTCACTGA   2700
TTAAGCATTG GTAACTGTCA GACCAAGTTT ACTCATATAT ACTTTAGATT GATTTAGCTT   2760
GAATTAATTC CCGGAAGAGA GTCAATTCAG GGTGGTGAAT ATGAAACCAG TAACGTTATA   2820
CGATGTCGCA GAGTATGCCG GTGTCTCTTA TCAGACCGTT TCCCGCGTGG TGAACCAGGC   2880
CAGCCACGTT TCTGCGAAAA CGCGGGAAAA AGTGGAAGCG GCGATGGCGG AGCTGAATTA   2940
CATTCCCAAC CGCGTGGCAC AACAACTGGC GGGCAAACAG TCGTTGCTGA TTGGCGTTGC   3000
```

-continued

```
CACCTCCAGT CTGGCCCTGC ACGCGCCGTC GCAAATTGTC GCGGCGATTA AATCTCGCGC    3060
CGATCAACTG GGTGCCAGCG TGGTGGTGTC GATGGTAGAA CGAAGCGGCG TCGAAGCCTG    3120
TAAAGCGGCG GTGCACAATC TTCTCGCGCA ACGCGTCAGT GGGCTGATCA TTAACTATCC    3180
GCTGGATGAC CAGGATGCCA TTGCTGTGGA AGCTGCCTGC ACTAATGTTC CGGCGTTATT    3240
TCTTGATGTC TCTGACCAGA CACCCATCAA CAGTATTATT TTCTCCCATG AAGACGGTAC    3300
GCGACTGGGC GTGGAGCATC TGGTCGCATT GGGTCACCAG CAAATCGCGC TGTTAGCGGG    3360
CCCATTAAGT TCTGTCTCGG CGCGTCTGCG TCTGGCTGGC TGGCATAAAT ATCTCACTCG    3420
CAATCAAATT CAGCCGATAG CGGAACGGGA AGGCGACTGG AGTGCCATGT CCGGTTTTCA    3480
ACAAACCATG CAAATGCTGA ATGAGGGCAT CGTTCCCACT GCGATGCTGG TTGCCAACGA    3540
TCAGATGGCG CTGGGCGCAA TGCGCGCCAT TACCGAGTCC GGGCTGCGCG TTGGTGCGGA    3600
TATCTCGGTA GTGGGATACG ACGATACCGA AGACAGCTCA TGTTATATCC CGCCGTCAAC    3660
CACCATCAAA CAGGATTTTC GCCTGCTGGG GCAAACCAGC GTGGACCGCT TGCTGCAACT    3720
CTCTCAGGGC CAGGCGGTGA AGGGCAATCA GCTGTTGCCC GTCTCACTGG TGAAAAGAAA    3780
AACCACCCTG GCGCCCAATA CGCAAACCGC CTCTCCCCGC GCGTTGGCCG ATTCATTAAT    3840
GCAGCTGGCA CGACAGGTTT CCCGACTGGA AAGCGGGCAG TGAGCGCAAC GCAATTAATG    3900
TCGAAAAACT TCATTTTTAA TTTAAAAGGA TCTAGGTGAA GATCCTTTTT GATAATCTCA    3960
TGACCAAAAT CCCTTAACGT GAGTTTTCGT TCCACTGAGC GTCAGACCCC GTAATAAGAT    4020
GATCTTCTTG AGATCGTTTT GGTCTGCGCG TAATCTCTTG CTCTGAAAAC GAAAAAACCG    4080
CCTTGCAGGG CGGTTTTTCG TATGATACAG GAGTAAAACC GCCGAAGCCC GGCGTAAGCC    4140
GGTACTGATT GATAGATTTC ACCTTACCCA TCCCCAGCCC TGCCAGACCA TACCCGCTTT    4200
CAGCCATGAG AGAGCTTCTG TGCGCGGTCG GAGTGGTCCC GACGAGGGTT TACCCGAAGT    4260
CGGGGCGTGT CTCCGCGTTA GCGGGCCGTG AGGGCCGCTT ACGAGCGTGT ACTGAGAACT    4320
TCCAGCGAGA AGACTGACAG CGATGAAGAT GTAGTTACAA CATTCATAAT TAAAAGCGAC    4380
TCTGTTCCGG CCCTTTGGGC CGGGGCGGGG CCGCTTTTCA GTTATGAGGG AGGGGCTTTG    4440
TGGTTTCGGT TCTGCGCTGG ACCGGGGTTT TTCTGGAGGT TGTTTTTGTG TGTTGTAACT    4500
AAAGTGGCTC CGGTCGGGGC CCGCCGCTTG CGGTGGGAGG TGCATATCTG TCTGTCCACA    4560
GGACAGGCAG TGAATAGGTT TTCTTTTTAA ATGAATGTAA TTAAGTAGTT TAAAGGAGAT    4620
ATAAACAGGT GTTAAAAGA TACATTGCAC CCTGTAAGAC TGGCGGCTGG CGCTTTATGA    4680
CATGAACGGT TGTAACCTTA TGGGGAAGTC CCTTGCAGTT AAATGTGGAT AAGCAAAATT    4740
CCCCGTCGCT GAGGCGTATT TTGTATTAAA AACAGGGGGA ATCGGATGCT CCAGAAGGTG    4800
GATGATGAGA TTGTTTTTTG CATGCGACGC TGTTTTTTTG TGCACCGGCG GGCTTCAGGC    4860
GTGCGGATGC CTCCGGCGCA GGCCGGATTA TTCTGAGGAG ATCACTTTCA GGGAGAAGCT    4920
GTGGCCAGCC GGCTGTAATT GCGGTTACGT GACAGAATCA TGCGCTCCTT CACACGACGC    4980
TCCACTTCGC GTTTTACCGC CTCACCATTA GCAGTGAAGC GTCCTTCCGA GATTTCACGG    5040
GTCAGCTGCC GTTTCACTAG GGTGACGATA TCCTGACGTT CTCTGTTCGC ATCACGACGC    5100
GCACGGGCAC GTTTTATTCC ACGGGACTGA AGCTCTGTCT GGTAACTGCG GAAACGCTCA    5160
CGCACAAAAC GCCAGGCTTT CGCTATCAGC TCATCCATAC CCAGGGTATC CAGCCCCTGC    5220
TTTTTGCGCT GTTTGTTTTC CCATTCAACA CGACTGCGGC GCGCAGCTGC CACTGCATCC    5280
TCAGACACAT CAAGGGCAGC AAACAGAGCC AGTGTGAACG TGATGTCGGT CGGAATGTAG    5340
CACCCGATAA GCGGGTCATA TTCCGTCTGG TAGGTAATCA GTCCCAGCTC TGACAGGAAC    5400
```

```
GTCAGGGCCC GGGTGGCACG GGTGATGGAG AGTTTTCCTG CACCGGACTC TGTCGCCAGT   5460

CCGCACTCAA TGGCCAGTGT GGTGATGGAA CACTGGACGC GGTTGGCCAG CGGGTCATAG   5520

TGGAAACACA GCCCCTGCAG CAGCGCATCA ATAGCCCGTC GACGCAGCAC CGGTGGCATG   5580

CGCCGACGCA GACCACGGGA ACGGGCATGC GCCACATGAA TGGCGAAATC AAAACGGGAG   5640

GTGAGGCCCA CCGCCTTTTC CATCGGTTTT TCGCGGAACT TCGGCGTTCC GGCACCTTCA   5700

CGGGGAGTGA ACACCGGATT CGGGTTCTTT ACCTGGCGGT AATACGTTTG GTGAAGATCA   5760

GTCACACCAT CCTGCACTTA CAATGCGCAG AAGGAGCGAG CACAGAAAGA AGTCTTGAAC   5820

TTTTCCGGGC ATATAACTAT ACTCCCCGCA TAGCTGAATT GTTGGCTATA CGGTTTAAGT   5880

GGGCCCCGGT AATCTTTTCG TACTCGCCAA AGTTGAAGAA GATTATCGGG TTTTTGCTT    5940

TTCTGGCTCC TGTAAATCCA CATCAGAACC AGTTCCTTGC CACCTTACGG CGTGGCAGCC   6000

ACAAAATTCC TTAAACGATC AGTAATCTAG CTAGCTACGC CACAAAGTAA AGTCTTTTAC   6060

TTTAGTATAT CCAGTCTCTG CAGTTCATCT TGATGATTT TCTCAACGAA CTGAGCCTGT    6120

GTTATCCCCT CTCTCTCGCA GTACTCAACC ATGAGATCGA TCTTTCAGAG GATTTTTGAC   6180

AAAAACTTTT ATCTCTTTGT GTGTAAGACG TTTTCTTGCA ACAGCGGCCA TTTGTTTCTC   6240

AGAGTCAGTC ATAGGCTTAC CTCTGCGCAC AAACCGCTTT TGACTCAATG AGGAAGTCAC   6300

TGCATTTTCT GTCTGCGACA TCTCGCCTCC TCAATACTCA AACAGGGATC GTTTCGCAGA   6360

GGATACTACA GTTTTTTGAA ATCAGCAACT TGAGAATTGT GACGAAGATC TTTAGCTGTC   6420

TTGGTTTGCC CAAAGCGCAT TGCATAATCT TTCAGGGTTA TGCGTTGTTC CATACAACCT   6480

CCTTAGTACA TGCAACCATT ATCACCGCCA GAGGTAAAAT AGTCAACACG CACGGTGTTA   6540

GATATTTATC CCTTGCGGTG ATAGATTTAA CGTATGAGCA CAAAAAGAA ACCATTAACA     6600

CAAGAGCAGC TTGAGGACGC ACGTCGCCTT AAAGCAATTT ATGAAAAAAA GAAAAATGAA   6660

CTTGGCTTAT CCCAGGAATC TGTCGCAGAC AAGATGGGGA TGGGGCAGTC AGGCGTTGGT   6720

GCTTTATTTA ATGGCATCAA TGCATTAAAT GCTTATAACG CCGCATTGCT TACAAAAATT   6780

CTCAAAGTTA GCGTTGAAGA ATTTAGCCCT TCAATCGCCA GAGAAATCTA CGAGATGTAT   6840

GAAGCGGTTA GTATGCAGCC GTCACTTAGA AGTGAGTATG AGTACCCTGT TTTTTCTCAT   6900

GTTCAGGCAG GGATGTTCTC ACCTAAGCTT AGAACCTTTA CCAAAGGTGA TGCGGAGAGA   6960

TGGGTAAGCA CAACCAAAAA AGCCAGTGAT TCTGCATTCT GGCTTGAGGT TGAAGGTAAT   7020

TCCATGACCG CACCAACAGG CTCCAAGCCA AGCTTTCCTG ACGGAATGTT AATTCTCGTT   7080

GACCCTGAGC AGGCTGTTGA GCCAGGTGAT TTCTGCATAG CCAGACTTGG GGGTGATGAG   7140

TTTACCTTCA AGAAACTGAT CAGGGATAGC GGTCAGGTGT TTTTACAACC ACTAAACCCA   7200

CAGTACCCAA TGATCCCATG CAATGAGAGT TGTTCCGTTG TGGGGAAAGT TATCGCTAGT   7260

CAGTGGCCTG AAGAGACGTT TGGCTGATCG GCAAGGTGTT CTGGTCGGCG CATAGCTGAT   7320

AACAATTGAG CAAGAATCTT CATCGAATTA GGGGAATTTT CACTCCCCTC AGAACATAAC   7380

ATAGTAAATG GATTGAATTA TGAAGAATGG TTTTTATGCG ACTTACCGCA GCAAAAATAA   7440

AGGGAAAGAT AAGCCTAGTG CTACTTGAGG GTATACCGCA AGAATATACG CAAGCGTCAG   7500

GATAGCTGCC AAAGCCGCAA GGAATTTACC AACCTTCTTA AACATAAAGT GTCTCCTTAT   7560

AAACGCAGAA AGGCCCACCC GAAGGTGAGC CAGTGTGATT ACATTTTCTC TTGAGGGTTG   7620

TCCTCGGTGC CACGGAACAT TACGAACGAT GGGTGCCGCA AAGAGCCATC AGGTGTTTCC   7680

TCCATGTAGC TAATTTGACA CGCCCAGCCA TCGTAAGGGT TAATAGTAAT TCGAGCTCGG   7740
```

-continued

| | | | | | |
|---|---|---|---|---|---|
| TACCCGGGGA | TCCTCTAGAG | CTCGAGGCCT | CATATGGATC | CACGTGAATT | CGTAATCATG | 7800
| TCATAGCTGT | TTCCTGTGTG | AAATTGTTAT | CCGCTCACAA | TTCCACACAA | CATACGAGCC | 7860
| GGAAGCATAA | AGTGTAAAGC | CTGGGGTGCC | TAATGAGTGA | GCTAACTCAC | ATTACTAGAG | 7920
| TC | | | | | | 7922

We claim:

1. A construct comprising an rbcLS promoter of Synechococcus and a lacZ promoter of *Escherichia coli* operatively linked to DNA fragments encoding pdc and adh enzymes obtained from *Zymomonas mobilis*.

2. A construct comprising an rbcLS promoter of Synechococcus and a lacZ promoter of *Escherichia coli* operatively linked to DNA encoding pdc and adh enzymes obtained from *Zymomonas mobilis*.

3. A construct according to claim 1, wherein said DNA fragments encoding the pdc enzyme is SEQ ID.NO.5.

4. A construct according to claim 1 wherein said DNA fragments encoding the adh enzyme is SEQ.ID NO.6.

5. A construct selected from the group consisting of pCB4-Rpa, pCB4-LRpa, pCB4-LR(TF)pa and pCB4-CPpa.

6. Genetically modified Cyanobacteria containing a temperature inducible construct comprising DNA fragments encoding pyruvate decarboxylase (pdc) and alcohol dehydrogenase (adh) enzymes obtained from the *Zymomonas mobilis* plasmid pLOI295 wherein said construct is pCB4-CPpa and said Cyanobacteria are capable of producing ethanol photosynthetically via a carbohydrate reserve.

7. Genetically modified Cyanobacteria according to claim 6 wherein said Cyanobacteria are transformable strains of Synechococcus.

8. Genetically modified Cyanobacteria according to claim 7 wherein the Cyanobacteria are Synechococcus PCC 7942.

9. Genetically modified Cyanobacteria according to claim 6 produced according to the following steps:

a. selecting an appropriate promoter;
b. ligating said promoter to pdc and adh encoding DNA sequences;
c. cloning said ligated sequences comprising the promoter, pdc and adh sequences into an appropriate construct;
d. transforming said construct into said Cyanobacteria.

10. Genetically modified Cyanobacteria according to claim 9 wherein said Cyanobacteria is Synechococcus PCC 7942 or other transformable strains of Synechococcus.

11. Genetically modified Cyanobacteria containing a construct comprising DNA fragments encoding pyruvate decarboxylase (pdc) and alcohol dehydrogenase (adh) enzymes obtained from the *Zymomonas mobilis* plasmid pLOI295, said Cyanobacteria being capable of producing ethanol photosynthetically via a carbohydrate reserve and are produced according to the following steps:

a. selecting an appropriate promoter;
b. ligating said promoter to pdc and adh encoding DNA sequences;
c. cloning said ligated sequences comprising the promoter, pdc and adh sequences into an appropriate construct, said construct selected from the group consisting of pCB4-Rpa, pCB4-LRpa and pCB4-LR(TF)pa;
d. transforming said construct into said Cyanobacteria, wherein said Cyanobacteria is Synechococcus PCC 7942 or other transformable strains of Synechococcus.

* * * * *